(12) United States Patent
Saikia et al.

(10) Patent No.: US 11,535,837 B2
(45) Date of Patent: Dec. 27, 2022

(54) MANNANASE VARIANTS AND POLYNUCLEOTIDES ENCODING SAME

(71) Applicant: Novozymes A/S, Bagsvaerd (DK)

(72) Inventors: Rakhi Saikia, Bangalore (IN); Naveen Shivanand Raikar, Bangalore (IN); Padmavathi Balumuri, Bangalore (IN); Jens Erik Nielsen, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 267 days.

(21) Appl. No.: 17/041,522

(22) PCT Filed: Mar. 27, 2019

(86) PCT No.: PCT/EP2019/057739
§ 371 (c)(1),
(2) Date: Sep. 25, 2020

(87) PCT Pub. No.: WO2019/185726
PCT Pub. Date: Oct. 3, 2019

(65) Prior Publication Data
US 2021/0024910 A1    Jan. 28, 2021

(30) Foreign Application Priority Data
Mar. 29, 2018  (IN) .............................. 201841011883

(51) Int. Cl.
*C12N 9/24* (2006.01)
*C11D 3/386* (2006.01)

(52) U.S. Cl.
CPC ........ *C12N 9/2494* (2013.01); *C11D 3/38636* (2013.01); *C12Y 302/01078* (2013.01)

(58) Field of Classification Search
None
See application file for complete search history.

(56) References Cited

FOREIGN PATENT DOCUMENTS

| WO | 1999/64619 | A1 | 12/1999 |
| WO | 2016007929 | A2 | 1/2016 |
| WO | WO2016/007929 | * | 1/2016 |
| WO | 2016054176 | A1 | 4/2016 |
| WO | 2017079751 | A1 | 5/2017 |
| WO | 2017079756 | A1 | 5/2017 |

OTHER PUBLICATIONS

Ademark et al, 1998, J Biotechnol, vol. 63, pp. 199-210.
Araujo et al, 1990, J Appl Bacteriol, vol. 68, pp. 253-261-.
Bewley et al, 1997, Planta, vol. 203, pp. 454-459.
Chauhan et al, 2012, Appl Microbiol Biotechnol, vol. 93, pp. 1817-1830.
Dhawan et al, 2007, CRC Critical reviews in biotechnology, vol. 27, No. 4, pp. 197-216.
Dutta et al, 1997, Plant Physiol, vol. 113, pp. 155-161.
Groot et al, 2017, EBI Accession No. A0A1H7IJ0.
Halstead et al, 2000, FEMS Microbiol Lett, vol. 192, pp. 197-203.
Henrissat, 1991, Biochem J, vol. 280, No. 2, pp. 309-316.
Lee et al, 2003, Poultry Science , vol. 82, pp. 1925-1931.
McCutchen et al, 1996, Biotechnol Bioeng, vol. 52, pp. 332-339.
Moreira et al, 2008, Appl Microbiol Biotechnol, vol. 79, pp. 165-178.
Puchart et al, 2004, Biochim Biophys Acta, vol. 1674, pp. 239-250.
Suurnakki et al, 1997, Adv Biochem Eng Biotechnol , vol. 57, pp. 261-287.
Xu et al, 2002, Eur J Biochem, vol. 269, pp. 1753-1760.
WO 2016-007929 A2—EBI Accession No. BCK93905.
WO 2016-007929 A2—EBI Accession No. BCK93993.
WO 2017-079751 A1—EBI Accession No. BDW54902.
WO 2017-079751 A1—EBI Accession No. BDW54912.
WO 2017-202887 A1—EBI Accession No. BEQ91571.

* cited by examiner

*Primary Examiner* — Suzanne M Noakes
*Assistant Examiner* — Jae W Lee
(74) *Attorney, Agent, or Firm* — Kelly Reynolds

(57) ABSTRACT

The present invention relates to mannanase variants. The present invention also relates to polynucleotides encoding the variants; nucleic acid constructs, vectors, and host cells comprising the polynucleotides; and methods of using the variants.

13 Claims, No Drawings
Specification includes a Sequence Listing.

SEQUENCE LISTING

```
<160> NUMBER OF SEQ ID NOS: 5

<210> SEQ ID NO 1
<211> LENGTH: 325
<212> TYPE: PRT
<213> ORGANISM: Paenibacillus sp
<220> FEATURE:
<221> NAME/KEY: SIGNAL
<222> LOCATION: (1)..(28)
<220> FEATURE:
<221> NAME/KEY: mat_peptide
<222> LOCATION: (29)..(325)

<400> SEQUENCE: 1

Met Lys Gln Gln Lys Arg Leu Tyr Ala Arg Leu Leu Thr Leu Leu Phe
            -25                 -20                 -15

Ala Leu Ile Phe Leu Leu Pro His Ser Ala Ala Ala Met Ala Thr Gly
        -10                  -5                  -1   1

Phe Tyr Val Ser Gly Asn Lys Leu Tyr Asp Ser Thr Gly Lys Pro Phe
  5                  10                  15                  20
```

Val Met Arg Gly Val Asn His Gly His Ser Trp Phe Lys Asn Asp Leu
            25                  30                  35

Asn Thr Ala Ile Pro Ala Ile Ala Lys Thr Gly Ala Asn Thr Val Arg
            40                  45                  50

Ile Val Leu Ser Asn Gly Ser Leu Tyr Thr Lys Asp Asp Leu Asn Ala
            55                  60                  65

Val Lys Asn Ile Ile Asn Val Val Asn Gln Asn Lys Met Ile Ala Val
            70                  75                  80

Leu Glu Val His Asp Ala Thr Gly Lys Asp Asp Tyr Asn Ser Leu Asp
85                  90                  95                  100

Ala Ala Val Asn Tyr Trp Ile Ser Ile Lys Glu Ala Leu Ile Gly Lys
                105                 110                 115

Glu Asp Arg Val Ile Val Asn Ile Ala Asn Glu Trp Tyr Gly Thr Trp
                120                 125                 130

Asn Gly Ser Ala Trp Ala Asp Gly Tyr Lys Lys Ala Ile Pro Lys Leu
                135                 140                 145

Arg Asn Ala Gly Ile Lys Asn Thr Leu Ile Val Asp Ala Ala Gly Trp
        150                 155                 160

Gly Gln Phe Pro Gln Ser Ile Val Asp Tyr Gln Ser Val Phe Ala
165                 170                 175                 180

Ala Asp Ser Gln Lys Asn Thr Val Phe Ser Ile His Met Tyr Glu Tyr
                185                 190                 195

Ala Gly Lys Asp Ala Ala Thr Val Lys Ala Asn Met Glu Asn Val Leu
                200                 205                 210

Asn Lys Gly Leu Ala Leu Ile Ile Gly Glu Phe Gly Gly Tyr His Thr
        215                 220                 225

Asn Gly Asp Val Asp Glu Tyr Ala Ile Met Arg Tyr Gly Gln Glu Lys
        230                 235                 240

Gly Val Gly Trp Leu Ala Trp Ser Trp Tyr Gly Asn Ser Ser Gly Leu
245                 250                 255                 260

Asn Tyr Leu Asp Met Ala Thr Gly Pro Asn Gly Ser Leu Thr Ser Phe
                265                 270                 275

Gly Asn Thr Val Val Asn Asp Tyr Gly Ile Lys Asn Thr Ser Gln
        280                 285                 290

Lys Ala Gly Ile Phe
        295

<210> SEQ ID NO 2
<211> LENGTH: 297
<212> TYPE: PRT
<213> ORGANISM: Paenibacillus sp

<400> SEQUENCE: 2

Met Ala Thr Gly Phe Tyr Val Ser Gly Asn Lys Leu Tyr Asp Ser Thr
1               5                   10                  15

Gly Lys Pro Phe Val Met Arg Gly Val Asn His Gly His Ser Trp Phe
            20                  25                  30

Lys Asn Asp Leu Asn Thr Ala Ile Pro Ala Ile Ala Lys Thr Gly Ala
            35                  40                  45

Asn Thr Val Arg Ile Val Leu Ser Asn Gly Ser Leu Tyr Thr Lys Asp
        50                  55                  60

Asp Leu Asn Ala Val Lys Asn Ile Ile Asn Val Val Asn Gln Asn Lys
65                  70                  75                  80

Met Ile Ala Val Leu Glu Val His Asp Ala Thr Gly Lys Asp Asp Tyr

```
                    85                  90                  95
Asn Ser Leu Asp Ala Ala Val Asn Tyr Trp Ile Ser Ile Lys Glu Ala
                100                 105                 110
Leu Ile Gly Lys Glu Asp Arg Val Ile Val Asn Ile Ala Asn Glu Trp
                115                 120                 125
Tyr Gly Thr Trp Asn Gly Ser Ala Trp Ala Asp Gly Tyr Lys Lys Ala
                130                 135                 140
Ile Pro Lys Leu Arg Asn Ala Gly Ile Lys Asn Thr Leu Ile Val Asp
145                 150                 155                 160
Ala Ala Gly Trp Gly Gln Phe Pro Gln Ser Ile Val Asp Tyr Gly Gln
                165                 170                 175
Ser Val Phe Ala Ala Asp Ser Gln Lys Asn Thr Val Phe Ser Ile His
                180                 185                 190
Met Tyr Glu Tyr Ala Gly Lys Asp Ala Ala Thr Val Lys Ala Asn Met
                195                 200                 205
Glu Asn Val Leu Asn Lys Gly Leu Ala Leu Ile Ile Gly Glu Phe Gly
                210                 215                 220
Gly Tyr His Thr Asn Gly Asp Val Asp Glu Tyr Ala Ile Met Arg Tyr
225                 230                 235                 240
Gly Gln Glu Lys Gly Val Gly Trp Leu Ala Trp Ser Trp Tyr Gly Asn
                245                 250                 255
Ser Ser Gly Leu Asn Tyr Leu Asp Met Ala Thr Gly Pro Asn Gly Ser
                260                 265                 270
Leu Thr Ser Phe Gly Asn Thr Val Val Asn Asp Thr Tyr Gly Ile Lys
                275                 280                 285
Asn Thr Ser Gln Lys Ala Gly Ile Phe
                290                 295

<210> SEQ ID NO 3
<211> LENGTH: 326
<212> TYPE: PRT
<213> ORGANISM: Bacillus bogoriensis
<220> FEATURE:
<221> NAME/KEY: SIGNAL
<222> LOCATION: (1)..(28)
<220> FEATURE:
<221> NAME/KEY: mat_peptide
<222> LOCATION: (29)..(326)

<400> SEQUENCE: 3

Met Lys Gln Gln Lys Arg Leu Tyr Ala Arg Leu Leu Thr Leu Leu Phe
                -25                 -20                 -15
Ala Leu Ile Phe Leu Leu Pro His Ser Ala Ala Ala Ala Asn Ser Gly
            -10                  -5                  -1  1
Phe Tyr Val Ser Gly Thr Thr Leu Tyr Asp Ala Asn Gly Asn Pro Phe
5                   10                  15                  20
Val Met Arg Gly Ile Asn His Gly His Ala Trp Tyr Lys Asp Gln Ala
                25                  30                  35
Thr Thr Ala Ile Glu Gly Ile Ala Asn Thr Gly Ala Asn Thr Val Arg
                40                  45                  50
Ile Val Leu Ser Asp Gly Gly Gln Trp Thr Lys Asp Asp Ile His Thr
                55                  60                  65
Val Arg Asn Leu Ile Ser Leu Ala Glu Asp Asn His Leu Val Ala Val
                70                  75                  80
Leu Glu Val His Asp Ala Thr Gly Tyr Asp Ser Ile Ala Ser Leu Asn
85                  90                  95                  100
```

```
Arg Ala Val Asp Tyr Trp Ile Glu Met Arg Ser Ala Leu Ile Gly Lys
                105                 110                 115

Glu Asp Thr Val Ile Ile Asn Ile Ala Asn Glu Trp Phe Gly Ser Trp
            120                 125                 130

Glu Gly Asp Ala Trp Ala Asp Gly Tyr Lys Gln Ala Ile Pro Arg Leu
            135                 140                 145

Arg Asn Ala Gly Leu Asn His Thr Leu Met Val Asp Ala Ala Gly Trp
        150                 155                 160

Gly Gln Phe Pro Gln Ser Ile His Asp Tyr Gly Arg Glu Val Phe Asn
165                 170                 175                 180

Ala Asp Pro Gln Arg Asn Thr Met Phe Ser Ile His Met Tyr Glu Tyr
                185                 190                 195

Ala Gly Gly Asn Ala Ser Gln Val Arg Thr Asn Ile Asp Arg Val Leu
            200                 205                 210

Asn Gln Asp Leu Ala Leu Val Ile Gly Glu Phe Gly His Arg His Thr
        215                 220                 225

Asn Gly Asp Val Asp Glu Ala Thr Ile Met Ser Tyr Ser Glu Gln Arg
    230                 235                 240

Gly Val Gly Trp Leu Ala Trp Ser Trp Lys Gly Asn Gly Pro Glu Trp
245                 250                 255                 260

Glu Tyr Leu Asp Leu Ser Asn Asp Trp Ala Gly Asn Asn Leu Thr Ala
                265                 270                 275

Trp Gly Asn Thr Ile Val Asn Gly Pro Tyr Gly Leu Arg Glu Thr Ser
            280                 285                 290

Arg Leu Ser Thr Val Phe
        295

<210> SEQ ID NO 4
<211> LENGTH: 298
<212> TYPE: PRT
<213> ORGANISM: Bacillus bogoriensis

<400> SEQUENCE: 4

Ala Asn Ser Gly Phe Tyr Val Ser Gly Thr Thr Leu Tyr Asp Ala Asn
1               5                   10                  15

Gly Asn Pro Phe Val Met Arg Gly Ile Asn His Gly His Ala Trp Tyr
                20                  25                  30

Lys Asp Gln Ala Thr Thr Ala Ile Glu Gly Ile Ala Asn Thr Gly Ala
            35                  40                  45

Asn Thr Val Arg Ile Val Leu Ser Asp Gly Gly Gln Trp Thr Lys Asp
        50                  55                  60

Asp Ile His Thr Val Arg Asn Leu Ile Ser Leu Ala Glu Asp Asn His
65                  70                  75                  80

Leu Val Ala Val Leu Glu Val His Asp Ala Thr Gly Tyr Asp Ser Ile
                85                  90                  95

Ala Ser Leu Asn Arg Ala Val Asp Tyr Trp Ile Glu Met Arg Ser Ala
            100                 105                 110

Leu Ile Gly Lys Glu Asp Thr Val Ile Ile Asn Ile Ala Asn Glu Trp
        115                 120                 125

Phe Gly Ser Trp Glu Gly Asp Ala Trp Ala Asp Gly Tyr Lys Gln Ala
130                 135                 140

Ile Pro Arg Leu Arg Asn Ala Gly Leu Asn His Thr Leu Met Val Asp
145                 150                 155                 160

Ala Ala Gly Trp Gly Gln Phe Pro Gln Ser Ile His Asp Tyr Gly Arg
                165                 170                 175
```

```
Glu Val Phe Asn Ala Asp Pro Gln Arg Asn Thr Met Phe Ser Ile His
            180                 185                 190

Met Tyr Glu Tyr Ala Gly Gly Asn Ala Ser Gln Val Arg Thr Asn Ile
            195                 200                 205

Asp Arg Val Leu Asn Gln Asp Leu Ala Leu Val Ile Gly Glu Phe Gly
210                 215                 220

His Arg His Thr Asn Gly Asp Val Asp Glu Ala Thr Ile Met Ser Tyr
225                 230                 235                 240

Ser Glu Gln Arg Gly Val Gly Trp Leu Ala Trp Ser Trp Lys Gly Asn
                245                 250                 255

Gly Pro Glu Trp Glu Tyr Leu Asp Leu Ser Asn Asp Trp Ala Gly Asn
            260                 265                 270

Asn Leu Thr Ala Trp Gly Asn Thr Ile Val Asn Gly Pro Tyr Gly Leu
            275                 280                 285

Arg Glu Thr Ser Arg Leu Ser Thr Val Phe
            290                 295

<210> SEQ ID NO 5
<211> LENGTH: 269
<212> TYPE: PRT
<213> ORGANISM: Bacillus subtilis

<400> SEQUENCE: 5

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240
```

```
Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265
```

MANNANASE VARIANTS AND POLYNUCLEOTIDES ENCODING SAME

CROSS-REFERENCE TO RELATED APPLICATIONS

This application is a 35 U.S.C. 371 national application of international application no. PCT/EP2019/057739 filed Mar. 27, 2019 which claims priority or the benefit under 35 U.S.C. 119 of Indian application no. 201841011883 filed Mar. 29, 2018, the contents of which are fully incorporated herein by reference.

REFERENCE TO A SEQUENCE LISTING

The instant application contains a Sequence Listing which has been submitted in ASCII format via EFS-Web and is hereby incorporated by reference in its entirety. Said ASCII copy, created on Mar. 27, 2019 is named 14589-WO-PCT SQ listing_ST25.txt and is 13 KB in size.

BACKGROUND OF THE INVENTION

Field of the Invention

The present invention relates to mannanase variants exhibiting mannanase activity, compositions comprising the mannanase variants, polynucleotides encoding the variants, methods of producing the variants, and methods of using the variants.

Description of the Related Art

Endo-1,4-mannanases (EC 3.2.1.78) are involved in the random hydrolysis of (1→4)-β-D-mannosidic linkages in mannans, galactomannans, glucomannans and galactoglucomannans (Ademark et al. (1998) J. Biotechnol. 63:199-210).

Mannan containing polysaccharides are often a major component of the hemicellulose fraction in woods, both softwood and hardwood.

Essentially unsubstituted linear beta-1,4-mannan is found in fruits of several palm trees, such as palm kernels and coconuts. Unsubstituted beta-1,4-mannan which is present e.g. in ivory nuts resembles cellulose in the conformation of the individual polysaccharide chains, and is water-insoluble. In leguminous seeds, water-soluble galactomannan is the main storage carbohydrate comprising up to 20% of the total dry weight. See Moreira et al., (2008) Appl. Microbiol. Biotechnol. 79:165-178. Galactomannans have a linear beta-1,4-mannan backbone substituted with single alpha-1,6-galactose, optionally substituted with acetyl groups. Glucomannans are linear polysaccharides with a backbone of beta-1,4-linked mannose and glucose alternating in a more or less regular manner, the backbone optionally being substituted with galactose and/or acetyl groups. Mannans, galactomannans, glucomannans and galactoglucomannans glucomannan backbones with branched galactose) contribute to more than 50% of the softwood hemicellulose. Moreover, the cellulose of many red algae contains a significant amount of mannose.

Mannanases have been identified in several *Bacillus* and *Paenibacillus* organisms, but also from other bacteria, fungi, plants, and animals. See, Araujo A. et al., (1990) J. App. Bacteriol. 68:253-261; Dutta S. et al., (1997) Plant Physiol. 113: 155-161; Puchar V. et al, (2004) Biochim. Biophys. Acta 1674:239-250; Chauhan P. K. et al. (2012) Appl. Microbiol. Biotechnol. 93:1817-1830. Genes encoding these enzymes from a number of organisms have also been cloned and sequenced, many if not all have been classified also as members of glycosyl hydrolase (GH) family 5 or 26, based on their sequences. See, e.g., Bewley D. J., (1997) Planta 203:454-459; Halstead J. R. et al., (2000) FEMS Microl. Lett. 192: 197-203; Xu B. et al., (2002) Eur. J. Biochem. 269: 1753-1760; Henrissat, B. (1991) Biochem. J. 280:309-316.

Beta-mannanases have been used in commercial applications in, for example, industries such as the paper and pulp industry, foodstuff and feed industry, pharmaceutical industry and energy industry. Lee J. T., et al., (2003) Poult. Sci. 82: 1925-1931; McCutchen M. C., et al., (1996) Biotechnol. Bioeng. 52:332-339; Suurnakki A., et al., (1997) Adv. Biochem. Eng. Biotechnol, 57:261-287.

Within the household care industry, it has been known to use mannanases in e.g. laundry detergents. In WO 1999/064619 an alkaline mannanase, which exhibits mannanase activity also in the alkaline pH range when applied in cleaning compositions, is disclosed.

In WO 2016/054176 other mannanases exhibiting beta-mannanase activity are disclosed.

However, mannanases with improved stability, in particular when used in detergents, have not been disclosed in the prior art. As can be seen from the data herein disclosed, the stability of a wild-type mannanase can be significantly improved by protein engineering. Viewed from a commercial side, providing a mannanase having an improved stability, will have a great impact for the detergent producing industry.

Thus, it is the object of the present invention to provide mannanase variants with improved stability compared to its parent polypeptide.

SUMMARY OF THE INVENTION

The present invention relates to an isolated mannanase variant, or recombinant polypeptide or an active fragment thereof, wherein comprising a modification at one or more positions corresponding to a position selected from the positions 8, 9, 11, 13, 18, 21, 34, 37, 45, 47, 65, 100, 101, 104, 107, 108, 110, 114, 115, 116, 132, 133, 142, 147, 152, 154, 164, 169, 173, 174, 176, 177, 180, 183, 185, 196, 199, 201, 202, 205, 206, 210, 215, 226, 229, 231, 239, 243, 245, 257, 260, 267, 270, 275, 278, 282, 283, 284, 288, 292, 293, and 295 of the polypeptide of SEQ ID NO: 2, wherein each modification is independently a substitution, insertion, or deletion, wherein said variant has at least 59%, e.g. at least 60%, e.g. at least 65%, e.g., at least 70%, at least 75%, at least 80%, at least 85%, at least 90%, at least 95%, at least 96%, at least 97%, at least 98%, or at least 99%, but less than 100% sequence identity to the polypeptide of SEQ ID NO: 1, the polypeptide of SEQ ID NO: 2, the polypeptide of SEQ ID NO: 3, or the polypeptide of SEQ ID NO: 4, and wherein said variant, polypeptide or fragment has mannanase activity.

The present invention also relates to a composition comprising a variant as herein disclosed, use of such a composition in a domestic or industrial cleaning process, an isolated polynucleotide encoding the variants; nucleic acid constructs, vectors, and host cells comprising the polynucleotides; and methods of producing the variants as well as methods of dishwashing or laundering in automatic machines using a composition herein disclosed.

Definitions

Before the invention is described in further details, it is to be understood that the present variants, compositions and methods are not limited to particular embodiments described, as such may, of course, differ. It is also to be understood that the terminology used herein is for the purpose of describing particular embodiments only, and is not intended to be limiting, since the scope of the present invention will be limited only by the appended claims.

Thus, prior to discussing the invention in further detail, the following terms will first be defined. In accordance with the detailed description, the following abbreviations and definitions apply. Note that the singular forms "a", "an", and "the" include plural referents unless the context clearly indicates otherwise. Thus, for example, reference to "an enzyme" includes a plurality of such enzymes, and reference to "the dosage" includes reference to one or more dosages and equivalents thereof known to those skilled in the art, and so forth.

Certain ranges are presented herein with numerical values being preceded by the term "about". The term "about" as used herein, is to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, in connection with a numerical value, the term "about" refers to a range of −10% to +10% of the numerical value, unless term is otherwise specifically defined in context. In another example, the phrase a "pH value of about 9" refers to pH values of from 8.1 to 9.9, unless the pH value is specifically defined otherwise.

Mannanase: The term "mannanase" or "galactomannanase" as used herein refers to a mannanase enzyme defined as the officially named mannan endo-1,4-beta-mannosidase and having the alternative names beta-mannanase and endo-1,4-mannanase. The mannanase term also means a polypeptide or polypeptide domain of an enzymes that has the ability to catalyze the cleavage or hydrolysis of (1→4) beta-D-mannosidic linkages of mannans, galactomannans, glucomannans, and galactoglucomannans. Thus, it means that the mannanase has mannanase activity (EC 3.2.1.78). For purposes of the present invention, mannanase activity is determined according to the procedure described in the Examples. In one aspect, the variants of the present invention have at least 20%, e.g., at least 40%, at least 50%, at least 60%, at least 70%, at least 80%, at least 90%, at least 95%, or at least 100% of the mannanase activity of the polypeptide of SEQ ID NO: 1.

Additional enzyme: The term "additional enzyme" as used herein, refers to any enzyme or functionally active polypeptide, which may be an addition to e.g. a detergent composition, wherein one enzyme is already present. For example, a detergent composition comprising a mannanase or polypeptide having mannanase activity, may further comprise another enzyme. Such another or additional enzyme may be an enzyme having the same activity but in structure be different from the first enzyme in the composition. It may also be an enzyme having another activity, and thus, originate from another enzyme class.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Carbohydrate binding module: The term "carbohydrate binding module" means the region within a carbohydrate-active enzyme that provides carbohydrate-binding activity (Boraston et al., 2004, Biochem. J. 383: 769-781). A majority of known carbohydrate binding modules (CBMs) are contiguous amino acid sequences with a discrete fold. The carbohydrate binding module (CBM) is typically found either at the N-terminal or at the C-terminal extremity of an enzyme. Some CBMs are known to have specificity for cellulose. In one embodiment, the CBM is a family 35 CBM (Pfam PF16990) such as that disclosed in Tunnicliffe R B, Bolam D N, Pell G, Gilbert H J, Williamson M P; J Mol Biol. 2005; 347:287-296.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cleaning compositions: The term "cleaning compositions" as used herein, refers to admixtures of chemical ingredients that find use in the removal of undesired compounds, e.g. soils or stains, from items or surfaces to be cleaned, such as for example fabric, dishes, contact lenses, solid surfaces, hair, skin, and teeth. The compositions may be in the form of a liquid, gel, granule, powder, bar, paste, spray tablet, unit dose, sheet, or foam, depending on the surface or item to be cleaned and the desired form of the composition.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Comprising: The term "comprising" as used herein refers to, including, but not limited to, the component(s) or feature(s) after the term "comprising". The component(s) or feature(s) after the term "comprising" are required or mandatory, but the embodiment, may further include other non-mandatory or optional component(s) or feature(s).

Consisting of: The term "consisting of" as used herein refers to, including, and limited to, the component(s) or feature(s) after the term "consisting of". The component(s) or feature(s) after the term "consisting of" are therefore required or mandatory, and no other non-mandatory or optional component(s) or feature(s) are present in the embodiments.

Corresponding to: The term "corresponding to" as used herein, refers to a way of determining the specific amino acid of a sequence wherein reference is made to a specific amino acid sequence. E.g. for the purposes of the present invention, when references are made to specific amino acid positions, the skilled person would be able to align another amino acid sequence to said amino acid sequence that reference has been made to, in order to determine which specific amino acid may be of interest in said another amino acid sequence. Alignment of another amino acid sequence with e.g. the sequence as set forth in SEQ ID NO: 1, or any other amino acid sequence listed herein, has been described elsewhere herein. Alternative alignment methods may be used, and are well-known for the skilled person.

Detergent component: the term "detergent component" is defined herein to mean the types of chemicals which can be used in detergent compositions. Examples of detergent components are surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers. The detergent composition may comprise of one or more of any type of detergent component.

Detergent stability: The term "detergent stability" as used herein, refers to the stability of a specified detergent composition component, such as a hydrolytic enzyme, e.g. a mannanase variant, in a detergent composition mixture.

Dishwashing detergent composition: the term "dishwashing detergent composition" as used herein, refers to both a dishwashing detergent composition that may be used in automatic dishwashing and in manual dishwashing. The term refers thus, to all forms of compositions including, for example, granular, unit-dose, and liquid forms for cleaning dishware and cutlery, or any similar hard-surface item.

Expression: The term "expression" includes any step involved in the production of a variant including, but not limited to, transcription, post-transcriptional modification, translation, post-translational modification, and secretion.

Expression vector: The term "expression vector" as used herein, refers to a linear or circular DNA molecule that comprises a polynucleotide encoding a variant and is operably linked to control sequences that provide for its expression. Such control sequences may include a promotor to affect transcription, an optional operator sequence to control transcription, a sequence encoding suitable ribosome-binding sites on the mRNA, and sequence which control termination of transcription and translation. Different cell types may be used with different expression vectors.

Fabric: The term "fabric" as used herein, refers to, for example, woven, knit, and non-woven material, as well as staple fibers and filaments that can be converted to, for example, yarns and woven, knit and non-woven fabrics. The term encompasses material made from natural, as well as synthetic, e.g. manufactured, fibers.

Fragment: The term "fragment" means a polypeptide having one or more (e.g., several) amino acids absent from the amino and/or carboxyl terminus of a mature polypeptide; wherein the fragment has mannanase activity. In one aspect, a fragment contains at least 250 amino acid residues (e.g., amino acids 250 to 300 of SEQ ID NO: 2), at least 260 amino acid residues (e.g., amino acids 260 to 300 of SEQ ID NO: 2), at least 270 amino acid residues (e.g., amino acids 270 to 300 of SEQ ID NO: 2), or at least 285 amino acid residues (e.g., amino acids 285 to 300 of SEQ ID NO: 2. The fragment may be denoted as an "active fragment" herein, which means that the fragment maintains the activity as an intact polypeptide, such as a mannanase variant defined here.

Half-life improvement factor (HIF): The term "half-life improvement factor" or "HIF" as used herein, refers to the definition of the following formula: HIF=T½ (variant)/T½ (Wild-type), wherein T½ (variant)=(Ln (0.5)/Ln (RA-variant/100))*Time, wherein T½ (Wild-type)=(Ln (0.5)/Ln (RA-Wild-type/100))*Time, wherein "RA" is residual activity in percent and "Time" is the incubation time. A preferred way of calculating HIF is also described in example 4 herein. The half-life improvement factor may also be calculated based on the half-life of a parent mannanase (see the definition of "parent" below) that is not necessarily a wild-type.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication. Host cells useful in the present invention are generally prokaryotic or eukaryotic host, including any transformable microorganism in which expression can be achieved. Host cells are transformed or transfected with vectors constructed using recombinant DNA techniques. Such transformed host cells may be capable of one or both of replicating the vectors encoding the variant of the present invention and expressing the desired peptide product.

Improved property: The term "improved property" as used herein, refers to a characteristic associated with a variant that is improved compared to the parent. Such improved properties include, but are not limited to, catalytic efficiency, catalytic rate, in-detergent stability, chemical stability, oxidation stability, pH activity, pH stability, specific activity, stability under storage conditions, substrate binding, substrate cleavage, substrate specificity, substrate stability, surface properties, thermal activity, and thermostability.

In-detergent stability: The term "in-detergent stability" as used herein, refers to the stability of a mannanase enzyme, being both a wild-type, parent or variant, when it has been incubated in a detergent. For the purposes of the present invention, in-detergent stability may be determined as shown in the Examples.

Isolated: The term "isolated" as used herein, refers to a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Isolated polynucleotide: The term "isolated polynucleotide" means a polynucleotide that is modified by the hand of man. In one aspect, the isolated polynucleotide is at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Laundry detergent composition: the term "laundry detergent composition" as used herein, refers to a detergent composition that may be used in automatic laundry machines and in manual laundry setup. The term refers thus, to all forms of compositions including, for example, granular, unit-dose, and liquid forms for cleaning any type of fabric as defined elsewhere herein.

Mature polypeptide: The term "mature polypeptide" as used herein, refers to a polypeptide in its final form following translation and any post-translational modifications, such as N-terminal processing, C-terminal truncation, glycosylation, phosphorylation, etc. In one aspect, the mature polypeptide is amino acids 1 to 297 of SEQ ID NO: 1 based on the SignalP 3.0 predictions (Using neural networks (NN) and hidden Markov models (HMM) trained on Gram-positive bacteria) that predicts amino acids −28 to −1 of SEQ ID NO: 1 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" as used herein, refers to a polynucleotide that encodes a mature polypeptide having mannanase activity. In one aspect, the mature polypeptide coding sequence is nucleotides 218 to 1111 of SEQ ID NO: 3.

Mutant: The term "mutant" as used herein, refers to a polynucleotide encoding a variant.

Naturally-occurring amino acid: The term "naturally-occurring amino acid" residues as used herein, refers to anything such as polypeptide or nucleic acid sequences that is found in nature. Conversely, the ter "non-naturally occurring" refers to anything that is not found in nature, such as recombinant nucleic acids and synthetic polypeptides (produced in the laboratory or modifications of a wild-type sequence).

Nucleic acid construct: The term "nucleic acid construct" as used herein, refers to a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" as used herein, refers to a configuration in which a control sequence is placed at an appropriate position relative to the coding sequence of a polynucleotide such that the control sequence directs expression of the coding sequence. Thus, "operably linked" means that a regulatory region o functional domain having a known or desired activity, such as a promoter, terminator, signal sequence or enhancer region, is attached to or linked to a target (e.g., a gene or polypeptide) in such a manner as to allow the regulatory region or functional domain to control the expression, secretion or function of that target according to its known or desired activity.

Parent or parent mannanase: The term "parent", "parent mannanase" or "parent polypeptide" as used herein refers to any polypeptide with mannanase activity to which an modification is made to produce the enzyme variants of the present invention. In the present invention, it is to be understood, that a parent polypeptide refers to a naturally-occurring polypeptide that does not include a man-made substitution, insertion, or deletion at one or more amino acid positions. Similarly, the term "parent" with respect to a polynucleotide, refers to a naturally-occurring polynucleotide that does not include a man-made nucleoside change. However, a polynucleotide encoding a parent polypeptide is not limited to a naturally-occurring polynucleotide, but rather encompasses any polynucleotide encoding the parent polypeptide. The parent mannanase may be any mannanase having at least 60%, such as at least 62%, at least 65%, at least 70%, at least 75%, at least 80%, at least 85%, at least 90%, at least 95%, or 100% sequence identity to SEQ ID NO: 1 or 2.

Polypeptide or enzyme: The terms "polypeptide" and "enzyme" may be used interchangeably to refer to polymers of any length comprising amino acid residues linked by peptide bonds. The conventional one-letter or three-letter codes for amino acid residues are used herein. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.) as well as other modifications known in the art.

Protease: The term "protease" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The term "subtilases" refer to a sub-group of serine protease according to Siezen et al., *Protein Engng.* 4 (1991) 719-737 and Siezen et al. *Protein Science* 6 (1997) 501-523. Serine proteases or serine peptidases is a subgroup of proteases characterised by having a serine in the active site, which forms a covalent adduct with the substrate. Further the subtilases (and the serine proteases) are characterised by having two active site amino acid residues apart from the serine, namely a histidine and an aspartic acid residue. The subtilases may be divided into 6 sub-divisions, i.e. the Subtilisin family, the Thermitase family, the Proteinase K family, the Lantibiotic peptidase family, the Kexin family and the Pyrolysin family. The term "protease activity" means a proteolytic activity (EC 3.4). Proteases of the invention are endopeptidases (EC 3.4.21). The protease variants described herein have at least 20%, e.g., at least 40%, at least 50%, at least 60%, at least 70%, at least 80%, at least 90%, at least 95%, or at least 100% of the protease activity of the polypeptide of SEQ ID NO: 5.

Protease stability: The term "protease stability" as used herein, refers to the stability of a polypeptide, such as a mannanase enzyme, being both a wild-type, parent or variant, when it has been incubated in the presence of a protease.

For the purposes of the present invention, protease stability may be determined as described in the Examples.

Sequence identity: The relatedness between two amino acid sequences or between two nucleotide sequences is described by the parameter "sequence identity". As used herein, "percent (%) sequence identity" with respect to the amino acid or nucleotide sequence identified herein is defined as the percentage of amino acid residues or nucleotides in a candidate sequence that are identical with the amino acid residues or nucleotides in a mannanase sequence as set out in the mature sequence of SEQ ID NO: 1 or the sequence of SEQ ID NO: 2, or for nucleotides the sequence of SEQ ID NO: 3, after aligning the sequences and introducing gaps, if necessary, to achieve the maximum percent sequence identity, and not considering any conservative substitutions as part of the sequence identity.

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment–Total Number of Gaps in Alignment)

Surface cleaning: The term as used herein, refers to any type of cleaning, where a surface, which may be a hard surface or a soft, e.g. a fabric, surface. Such surfaces may be partially or fully covered by soil or stains of any naturel or non-naturel compound(s).

Surfactant: The term "surfactant" as used herein, refers to any compound generally recognized in the art as having surface active qualities. Surfactants generally include anionic, cationic, nonionic, amphoteric, and zwitterionic compounds, which are further described herein.

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and toweling. The textile may be cellulose based such as natural cellulosics, including cotton, flax/linen, jute, ramie, sisal or coir or manmade cellulosics (e.g. originating from wood pulp) including viscose/rayon, ramie, cellulose acetate fibers (tricell), lyocell or blends thereof. The textile or fabric may also be non-cellulose based such as natural polyamides including wool, camel, cashmere, mohair, rabbit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell). Fabric may be conventional washable laundry, for example stained household laundry. When the term fabric or garment is used, it is intended to include the broader term textiles as well.

Thermostability: The term "thermostability" as used herein, refers to polypeptides, such as mannanase variants, that retain a specified amount of enzymatic activity after exposure to elevated temperatures over a given period of time under conditions prevailing during the mannosidic, hydrolyzing, cleaning, or other process, for example, while exposed to elevated temperatures. Thermostability may also be determined after storage under elevated temperature conditions, such as described in the Examples herein. In some embodiments, the mannanase variant maintains at least about 50%, such as at least 60%, such as at least 70%, such as at least 75%, such as at least 80%, such as at least 85%, such as at least 90%, such as at least 95%, such as at least 96%, such as at least 97%, such as at least 98%, and such as at least 99% mannanase activity after exposure to elevated temperatures, for example at least about 45° C., at least 47° C., at least 50° C., at least 52° C., at least 53° C., at least 55° C., at least 57° C., at least 60° C., at least 63° C., at least 65° C., at least 67° C. over a given period of time, such as at least 5 min, at least 10 min, at least 15 min, at least 20 min, at least 25 min, at least 30 min, at least 35 min, at least 40 min, at least 45 min, at least 50 min, 60 min, 70 min, etc.

Variant: The term "variant" as used herein, refers to a polypeptide having mannanase activity comprising a modification, i.e., a substitution or deletion, at one position. A substitution means replacement of the amino acid occupying a position with a different amino acid; and a deletion means removal of the amino acid occupying a position. The variants of the present invention have at least 20%, e.g., at least 40%, at least 50%, at least 60%, at least 70%, at least 80%, at least 90%, at least 95%, or at least 100% of the mannanase activity of the mature polypeptide of SEQ ID NO: 1 or SEQ ID NO: 2.

Wild-type mannanase: The term "wild-type mannanase" as used herein, refers to a mannanase expressed by a naturally occurring microorganism, such as a bacterium, yeast, or filamentous fungus found in nature.

Conventions for Designation of Variants

For purposes of the present invention, the polypeptide disclosed in SEQ ID NO: 2 is used to determine the corresponding amino acid residue in another mannanase. The amino acid sequence of another mannanase is aligned with the polypeptide disclosed in SEQ ID NO: 2, and based on the alignment, the amino acid position number corresponding to any amino acid residue in the polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another mannanase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

When the other enzyme has diverged from the polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Multiple modifications. Variants comprising multiple modifications are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different modifications. Where different modifications can be introduced at a position, the different modifications are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:
"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to isolated mannanase variant, or recombinant polypeptide or an active fragment thereof, wherein comprising a modification at one or more positions corresponding to a position selected from the positions 8, 9, 11, 13, 18, 21, 34, 37, 45, 47, 65, 100, 101, 104, 107, 108, 110, 114, 115, 116, 132, 133, 142, 147, 152, 154, 164, 169, 173, 174, 176, 177, 180, 183, 185, 196, 199, 201, 202, 205, 206, 210, 215, 226, 229, 231, 239, 243, 245, 257, 260, 267, 270, 275, 278, 282, 283, 284, 288, 292, 293, and 295 of the polypeptide of SEQ ID NO: 2, wherein each modification is independently a substitution, insertion, or deletion, wherein said variant has at least 59%, e.g. at least 60%, e.g. at least 65%, e.g., at least 70%, at least 75%, at least 80%, at least 85%, at least 90%, at least 95%, at least 96%, at least 97%, at least 98%, or at least 99%, but less than 100% sequence identity to the polypeptide of SEQ ID NO:

1, the polypeptide of SEQ ID NO: 2, the polypeptide of SEQ ID NO: 3, or the polypeptide of SEQ ID NO: 4, and wherein said variant, polypeptide or fragment has mannanase activity.

The inventors of the present invention has found that a modification in one of the above listed positions provides a mannanase variant which have an improved stability compared to the parent mannanase, i.e. a mannanase not comprising a modification in any one of the listed positions. In particular, the stability may be observed as stability in detergent compositions or in the presence of a protease.

Unless specifically disclosed herein, the numbering of amino acid residues or positions, are done according to SEQ ID NO: 2.

The stability in detergent compositions may herein be referred to a "in detergent stability" or simply as "detergent stability" and falls under the definition elsewhere described herein. The terms may be used interchangeably, but constitute the same meaning and purpose for the present invention. The stability has been determined as described in the Examples.

In one embodiment, the alteration is a substitution.

In an embodiment, the alteration is a substitution, wherein said substitution of the naturally-occurring amino acid residue at the one or more positions is a substitution with a different amino acid residue wherein said substitution produces a mannanase variant having a Half-life Improvement Factor (HIF) of ≥1.0 for a measure of stability.

When the Half-life Improvement Factor (HIF) is more than 1.0, it means that the variant, polypeptide or fragment thereof tested has an improved property, such as improved stability, compared to the parent—or the starting—mannanase. Calculation of the Half-life Improvement Factor is described elsewhere herein. When the HIF is 1.0 it means that the measured property is not changed compared to the parent polypeptide. I.e. it is neither improved nor worsened compared to the parent polypeptide.

The substitution may be made in any one of the positions corresponding to positions: 8, 9, 11, 13, 18, 21, 34, 37, 45, 47, 65, 100, 101, 104, 107, 108, 110, 114, 115, 116, 132, 133, 142, 147, 152, 154, 164, 169, 173, 174, 176, 177, 180, 183, 185, 196, 199, 201, 202, 205, 206, 210, 215, 226, 229, 231, 239, 243, 245, 257, 260, 267, 270, 275, 278, 282, 283, 284, 288, 292, 293, and 295, wherein numbering is according to SEQ ID NO: 2.

In another embodiment, the alteration is an insertion.

In another embodiment, the alteration is an insertion, wherein said insertion of the naturally-occurring amino acid residue at the one position produces a mannanase variant having a Half-life Improvement Factor of >1.0 for a measure of stability. In another embodiment, the alteration is a deletion.

In another embodiment, the alteration is a deletion, wherein said deletion of the naturally-occurring amino acid residue at the one position produces a mannanase variant having a Half-life Improvement Factor of >1.0 for a measure of stability.

In one embodiment, the improved stability is detergent stability, thermostability, or stability towards protease cleavage. Thus, in one embodiment, the variant, polypeptide or fragment thereof, has an improved detergent stability, improved protease stability, and/or improved thermostability.

In one embodiment, the variant, polypeptide or fragment thereof comprises a different amino acid residue which is selected from the group consisting of A, C, D, E, F, G, H, I, K, L, M, N, P, Q, R, S, T, V, W, and Y, with the proviso that the different amino acid residue is different from the naturally-occurring amino acid residue.

In one embodiment, the variant, polypeptide, or fragments thereof comprises one or more of the following substitutions versus the mature polypeptide of SEQ ID NO: 1 or the polypeptide of SEQ ID NO: 2: S8A, S8D, S8E, S8I, S8K, S8L, S8M, S8R, S8T, G9L, G9Q, G9R, G9S, G9V, G9W, G9Y, K11A, K11M, K11Q, K11R, K11S, K11V, Y13F, Y13I, Y13M, K18A, K18F, K18L, K18Q, K18R, K18S, V21I, V21M, N34C, N34E, N37C, N37D, N37H, N37Y, N37G, N37Q, K45A, K45C, K45D, K45E, K45G, K45H, K45M, K45N, K45Q, K45R, K45S, K45T, G47A, G47D, G47L, G47Q, G47R, G47S, D65P, D100G, D100K, D100L, A101C, A101E, A101L, A101N, A101M, A101Q, N104I, N104L, N104T, N104V, N104Y, N104C, N104M, N104Q, N104W, I107C, I107V, S108A, S108D, S108E, S108F, S108G, S108V, S108W, S108Y, K110A, K110G, K110H, K110N, K110Q, K110C, K110L, K110M, K110S, K110T, I114A, I114C, I114F, I114G, I114H, I114L, I114M, I114N, I114Q, I114R, I114T, I114V, I114W, I114Y, G115C, G115D, G115F, G115H, G115M, G115R, G115W, K116L, K116M, K116V, W132O, W132E, W132M, W132Q, W132Y, N133A, N133C, N133D, N133F, N133G, N133K, N133L, N133M, N133R, N133S, N133T, N133W, N142F, N142L, K142C, K142E, K142I, K142M, K142Q, K142R, K142V, K142W, K142Y, K147H, K147I, K147S, G152C, G152E, G152M, G152N, G152Q, G152R, G152S, K154A, K154D, K154E, K154F, K154G, K154H, K154L, K154M, K154T, K154W, W164D, W164F, W164M, W164Q, W164S, W164Y, Q169A, Q169M, D173O, D173E, Y174F, Q176A, Q176O, Q176E, Q176G, Q176H, Q176K, Q176L, Q176M, Q176R, Q176P, S177A, S177C, S177D, S177E, S177H, S177I, S177L, S177Q, S177R, S177T, S177V, A180E, A180Q, S183A, S183D, S183E, S183G, S183I, S183P, S183R, S183V, S183W, K185G, K185S, K185T, K185V, K185W, K185Y, Y196I, Y196V, K199A, A201E, A202C, A202K, A202M, A202P, A202R, A202W, K205A, K205C, K205D, K205L, K205N, K205S, A206L, A206M, A206F, A206T, N210A, N210G, N210S, G215M, Y226C, Y226G, Y226K, Y226N, Y226Q, Y226R, Y226S, Y226T, Y226W, N229C, D231P, D231T, R239F, R239Y, E243F, E243M, E243W, G245A, G245C, G245E, G245K, G245M, G245N, G245Q, G245R, S257A, S257C, S257D, S257E, S257G, S257H, S257K, S257P, S257V, L260C, L260F, L260K, L260M, L260Q, L260Y, L260T, T267D, T267E, N270A, N270C, N270D, S275A, S275D, S275E, S275K, S275P, S275Q, S275T, S275V, N278C, N278D, N278E, N278H, N278W, N282C, N282F, N282Y, D283G, D283S, D283W, T284E, T284I, K288A, K288R, Q292E, Q292I, Q292M, Q292R, Q292V, K293I, K293L, K293P, K293R, and G295S, wherein numbering is according to SEQ ID NO: 2.

In one aspect of the invention, the variant, polypeptide, or fragments thereof comprises a modification in at least one of the following positions: 8, 9, 18, 34, 45, 47, 101, 104, 108, 114, 115, 116, 133, 142, 152, 177, 183, 201, 202, 205, 226, 229, 231, 239, 243, 245, 257, 260, 270, 275, 278, 282, 283, 292, and 293 and has a half-life improvement factor (HIF) of at least 1.2 when measured as detergent stability at a pH of 8.0.

In one embodiment, the variant, polypeptide, or fragments thereof comprises at least one of the following substitutions S8A, S8K, G9L, G9Q, G9S, G9V, G9W, G9Y, K18A, K18F, K18L, N34C, N34E, K45A, K45C, K45D, K45E, K45G, K45N, K45Q, K45S, G47L, G47Q, G47R, A101M, A101Q, N104Q, S108A, S108D, S108Y, I114A, I114C, I114H, I114L, I114N, I114Q, I114R, I114T, I114V, G115C, G115F, G115H, K116V, N133A, N133D, N133G, N133S, K142F, K142Y, G152C, G152E, G152N, G152Q, G152R, G152S, S177H, S177V, S183G, A201E, A202C, A202M, A202P, A202R, K205D, Y226C, Y226N, N229C, D231P, R239F, R239Y, E243W, G245E, G245N, G245Q, S257C, S257D, S257E, L260Y, N270D, S275A, S275D, S275E, S275P, S275T, N278D, N278E, N282C, N282Y, D283S, Q292E, Q292V, K293I, K293L, and K293P and has a half-life improvement factor (HIF) of at least 1.2 when measured as detergent stability at a pH of 8.0.

In one embodiment, the variant, polypeptide, or fragments thereof comprises a modification in at least one of the following positions: 9, 34, 45, 101, 108, 115, 133, 152, 201, 202, 205, 229, 231, 239, 245, 257, 260, 270, 275, 278, 282, 283, 292, and 293 and has a half-life improvement factor (HIF) of at least 1.4 when measured as detergent stability at a pH of 8.0.

In one embodiment, the variant, polypeptide, or fragments thereof comprises at least one of the following substitutions G9S, G9V, N34E, K45A, K45C, K45D, K45E, K45N, K45Q, K45S, A101M, S108D, S108Y, G115H, N133A, G152E, G152N, A201E, A202M, A202P, A202R, K205D, N229C, D231P, R239F, R239Y, G245E, G245Q, S257D, S257E, L260Y, N270D, S275D, S275E, S275T, N278E, N282C, N282Y, D283S, Q292V, K293L, and K293P and has a half-life improvement factor (HIF) of at least 1.4 when measured as detergent stability at a pH of 8.0.

In one embodiment, the variant, polypeptide, or fragments thereof comprises a modification in at least one of the following positions: 34, 45, 101, 108, 152, 205, 231, 239, 245, 257, 260, 270, 275, 283, 292, and 293 and has a half-life improvement factor of at least 1.6 when measured as detergent stability at a pH of 8.0.

In one embodiment, the variant, polypeptide, or fragments thereof comprises at least one of the following substitutions N34E, K45A, K45D, K45E, K45Q, A101M, S108D, G152N, K205D, D231P, R239F, R239Y, G245Q, S257D, S257E, L260Y, N270D, S275D, S275E, D283S, Q292V, and K293P and has a half-life improvement factor of at least 1.6 when measured as detergent stability at a pH of 8.0.

In one aspect of the present invention, the variant, polypeptide, or fragments thereof comprises a modification in at least one of the following positions: 47, 65, 101, 104, 108, 110, 114, 115, 116, 133, 142, 152, 154, 164, 174, 176, 180, 183, 185, 206, 226, 243, 245, 257, 260, 270, 275, 278, 282, 283, and 293 and has a half-life improvement factor of at least 1.3 when measured as protease stability at a pH of 8.0.

In one embodiment, the variant, polypeptide, or fragments thereof comprises at least one of the following substitutions G47R, D65P, A101E, A101M, N104I, N104V, S108E, S108V, K110H, K110S, K110T, I114A, I114G, G115M, K116V, N133A, N133C, N133D, N133F, N133G, N133M, N133R, N133S, N133W, K142C, K142E, K142Y, G152N, K154A, K154D, K154E, K154L, W164M, Y174F, Q176A, Q176K, Q176L, A180E, S183R, K185G, K185S, K185T, A206M, Y226G, E243M, E243W, G245E, G245Q, G245R, S257D, S257E, S257P, L260K, N270D, S275D, S275E, S275P, S275Q, N278E, N282F, N282Y, D283W, and K293L and has a half-life improvement factor of at least 1.3 when measured as protease stability at a pH of 8.0.

In one embodiment, the variant, polypeptide, or fragments thereof comprises a modification in at least one of the following positions: 47, 104, 108, 133, 142, 152, 154, 176, 183, 243, 257, 260, 270, 275, 278, 282, and 283 and has a half-life improvement factor of at least 1.5 when measured as protease stability at a pH of 8.0.

In one embodiment, the variant, polypeptide, or fragments thereof comprises at least one of the following substitutions G47R, N104V, S108E, N133A, N133C, N133D, K142Y, G152N, K154D, Q176K, S183R, E243W, S257D, S257E, S257P, L260K, N270D, S275D, S275E, S275P, S275Q, N278E, N282Y, and D283W and has a half-life improvement factor of at least 1.5 when measured as protease stability at a pH of 8.0.

In one aspect of the present invention, the variant, polypeptide, or fragments thereof comprises a modification in at least one of the following positions: 8, 11, 21, 34, 37, 45, 101, 108, 116, 132, 133, 142, 154, 164, 173, 176, 177, 180, 183, 196, 205, 210, 226, 239, 245, 257, 260, 270, 275, 278, 282, 283, 292, and 293 and has a half-life improvement factor of at least 1.2 when measured as thermostability at a pH of 8.0.

In one embodiment, the variant, polypeptide, or fragments thereof comprises at least one of the following substitutions S8E, K11M, K11V, V21I, N34E, N37C, N37D, N37G, N37H, N37Q, K45A, K45E, K45G, K45M, K45N, K45Q, K45R, A101C, A101E, A101L, A101M, A101Q, S108D, S108E, K116M, W132E, W132Q, W132Y, N133C, N133D, N133S, K142I, K142R, K154M, W164A, W164F, W164M, W164Q, W164S, W164Y, D173E, Q176E, S177C, S177D, S177E, S177Q, A180C, A180E, S183D, S183E, S183P, Y196I, Y196V, K205L, N210A, N210S, Y226G, Y226K, Y226N, Y226Q, Y226R, Y226S, Y226W, R239Y, G245C, G245Q, S257C, S257D, S257E, S257G, S257H, S257K, S257P, L260K, L260Q, N270D, S275A, S275D, S275E, S275P, N278D, N278E, N278W, N282Y, D283G, D283S, D283W, Q292V, K293I, K293L, K293P, and K293R and has a half-life improvement factor of at least 1.2 when measured as thermostability at a pH of 8.0.

In one embodiment, the variant, polypeptide, or fragments thereof comprises a modification in at least one of the following positions: 11, 21, 34, 37, 45, 101, 108, 116, 132, 133, 142, 154, 164, 176, 177, 180, 183, 196, 205, 210, 226, 245, 257, 260, 270, 275, 278, 282, 283, 292, and 293 and has a half-life improvement factor of at least 1.5 when measured as thermostability at a pH of 8.0.

In one embodiment, the variant, polypeptide, or fragment thereof comprises at least one of the following substitutions K11V, V21I, N34E, N37C, N37D, N37H, N37Q, K45A, K45E, K45G, K45N, K45Q, K45R, A101E, A101M, S108D, S108E, K116M, W132Q, N133C, N133D, K142Y, K154M, W164F, W164M, W164Q, W164S, W164Y, Q176E, S177D, S177E, A180C, A180E, S183D, S183E, S183P, Y196I, K205L, N210A, N210S, Y226G, Y226R, Y226S, G245C, G245Q, S257C, S257D, S257E, S257G, S257H, S257P, L260K, N270D, S275A, S275D, S275E, N278E, N282Y, D283G, D283S, Q292V, K293L, and K293P and has a half-life improvement factor of at least 1.5 when measured as thermostability at a pH of 8.0.

In one embodiment, the variant, polypeptide, or fragments thereof comprises a modification in at least one of the following positions: 11, 34, 37, 45, 101, 108, 116, 132, 133, 154, 164, 176, 177, 180, 183, 210, 226, 257, 270, 275, 278, and 293 and has a half-life improvement factor of at least 1.8 when measured as thermostability at a pH of 8.0.

In one embodiment, the variant, polypeptide, or fragments thereof comprises at least one of the following substitutions K11V, N34E, N37C, N37D, N37Q, K45A, K45E, K45Q, A101E, S108D, S108E, K116M, W132Q, N133C, N133D, K154M, W164S, W164Y, Q176E, S177D, S177E, A180E, S183P, N210A, N210S, Y226G, S257C, S257D, S257E, S257P, N270D, S275E, N278E, K293L, and K293P and has a half-life improvement factor of at least 1.8 when measured as thermostability at a pH of 8.0.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Gly, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

In another embodiment, the variant comprises or consists of a substitution in the position corresponding to position 8 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of A1G, A1V, A1I, A1M, A1W, A1S, A1T, A1C, A1Y, A1N, A1D, A1E, A1K, A1R, A1H, A1Q, and A1F.

In another embodiment, the variant comprises or consists of a substitution in the position corresponding to position 2 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of S8A, S8D, S8E, S8I, S8K, S8L, S8M, S8R, and S8T.

In another embodiment, the variant comprises or consists of a substitution in the position corresponding to position 9 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of G9L, G9Q, G9R, G9S, G9V, G9W, and G9Y.

In another embodiment, the variant comprises or consists of a substitution in the position corresponding to position 11 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of K11A, K11M, K11Q, K11R, K11S, and K11V.

In another embodiment, the variant comprises or consists of a substitution in the position corresponding to position 13 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of Y13F, Y13I, and Y13M.

In another embodiment, the variant comprises or consists of a substitution in the position corresponding to position 18 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of K18A, K18F, K18L, K18Q, K18R, and K18S.

In another embodiment, the variant comprises or consists of a substitution in the position corresponding to position 21 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of V21I and V21M.

In another embodiment, the variant comprises or consists of a substitution in the position corresponding to position 34 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of N34C and N34E.

In another embodiment, the variant comprises or consists of a substitution in the position corresponding to position 37 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group consisting of: N37C, N37D, N37H, N37Y, N37G, and N37Q.

In another embodiment, the variant comprises or consists of a substitution in the position corresponding to position 45 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of K45A, K45C, K45D, K45E, K45G, K45H, K45M, K45N, K45Q, K45R, K45S, and K45T.

In another embodiment, the variant comprises or consists of a substitution in the position corresponding to position 47 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of G47A, G47D, G47L, G47Q, G47R, and G47S.

In another embodiment, the variant comprises or consists of a substitution in the position corresponding to position 65 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is D65P.

In another embodiment, the variant comprises or consists of a substitution in the position corresponding to position 100 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of: D100G, D100K, and D100L.

In another embodiment, the variant comprises or consists of a substitution in the position corresponding to position 101 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of A101C, A101E, A101L, A101N, A101M, and A101Q.

In another embodiment, the variant comprises or consists of a substitution in the position corresponding to position 104 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of N104I, N104L, N104T, N104V, N104Y, N104C, N104M, N104Q, and N104W.

In another embodiment, the variant comprises or consists of a substitution in the position corresponding to position 107 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of I107C, and I107V.

In another embodiment, the variant comprises or consists of a substitution in the position corresponding to position 108 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of S108A, S108D, S108E, S108F, S108G, S108V, S108W, and S108Y.

In another embodiment, the variant comprises or consists of a substitution in the position corresponding to position 110 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of: K110A, K110G, K110H, K110N, K110Q, K110C, K110L, K110M, K110S, and K110T.

In another embodiment, the variant comprises or consists of a substitution in the position corresponding to position 114 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of I114A, I114C, I114F, I114G, I114H, I114L, I114M, I114N, I114Q, I114R, I114T, I114V, I114W, and I114Y.

In another embodiment, the variant comprises or consists of a substitution in the position corresponding to position 115 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of G115C, G115D, G115F, G115H, G115M, G115R, and G115W.

In another embodiment, the variant comprises or consists of a substitution in the position corresponding to position 116 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of K116L, K116M, and K116V.

In another embodiment, the variant comprises or consists of a substitution in the position corresponding to position 132 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of W132C, W132E, W132M, W132Q, and W132Y.

In another embodiment, the variant comprises or consists of a substitution in the position corresponding to position 133 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of N133A, N133C, N133D, N133F, N133G, N133K, N133L, N133M, N133R, N133S, N133T, and N133W.

In another embodiment, the variant comprises or consists of a substitution in the position corresponding to position 142 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group K142F, K142L, K142C, K142E, K142I, K142M, K142Q, K142R, K142V, K142W, and K142Y.

In another embodiment, the variant comprises or consists of a substitution in the position corresponding to position 147 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of K147H, K147I, and K147S.

In another embodiment, the variant comprises or consists of a substitution in the position corresponding to position 152 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of G152C, G152E, G152M, G152N, G152Q, G152R, and G152S.

In another embodiment, the variant comprises or consists of a substitution in the position corresponding to position 154 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of K154A, K154D, K154E, K154F, K154G, K154H, K154L, K154M, K154T, and K154W.

In another embodiment, the variant comprises or consists of a substitution in the position corresponding to position 164 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of W164D, W164F, W164M, W164Q, W164S, and W164Y.

In another embodiment, the variant comprises or consists of a substitution in the position corresponding to position 169 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of Q169A and Q169M.

In another embodiment, the variant comprises or consists of a substitution in the position corresponding to position 173 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of D173C and D173E.

In another embodiment, the variant comprises or consists of a substitution in the position corresponding to position 174 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is Y174F.

In another embodiment, the variant comprises or consists of a substitution in the position corresponding to position 176 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of Q176A, Q176C, Q176E, Q176G, Q176H, Q176K, Q176L, Q176M, Q176R, and Q176P.

In another embodiment, the variant comprises or consists of a substitution in the position corresponding to position 177 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of S177A, S177C, S177D, S177E, S177H, S177I, S177L, S177Q, S177R, S177T, and S177V.

In another embodiment, the variant comprises or consists of a substitution in the position corresponding to position 180 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of A180E and A180Q.

In another embodiment, the variant comprises or consists of a substitution in the position corresponding to position 183 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of S183A, S183D, S183E, S183G, S183I, S183P, S183R, S183V, and S183W.

In another embodiment, the variant comprises or consists of a substitution in the position corresponding to position 185 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of K185G, K185S, K185T, K185V, K185W, and K185Y.

In another embodiment, the variant comprises or consists of a substitution in the position corresponding to position 196 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of Y196I and Y196V.

In another embodiment, the variant comprises or consists of a substitution in the position corresponding to position 199 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is K199A.

In another embodiment, the variant comprises or consists of a substitution in the position corresponding to position 201 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is A201E.

In another embodiment, the variant comprises or consists of a substitution in the position corresponding to position 202 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of A202Q, A202K, A202M, A202P, A202R, and A202W.

In another embodiment, the variant comprises or consists of a substitution in the position corresponding to position 205 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of K205A, K205C, K205D, K205L, K205N, and K205S.

In another embodiment, the variant comprises or consists of a substitution in the position corresponding to position 206 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of A206L, A206M, A206F, and A206T.

In another embodiment, the variant comprises or consists of a substitution in the position corresponding to position 210 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of N210A, N210G, and N210S.

In another embodiment, the variant comprises or consists of a substitution in the position corresponding to position 215 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is G215M.

In another embodiment, the variant comprises or consists of a substitution in the position corresponding to position 226 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of Y226C, Y226G, Y226K, Y226N, Y226Q, Y226R, Y226S, Y226T, and Y226W.

In another embodiment, the variant comprises or consists of a substitution in the position corresponding to position 229 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is N229C.

In another embodiment, the variant comprises or consists of a substitution in the position corresponding to position 231 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of D231F and D231T.

In another embodiment, the variant comprises or consists of a substitution in the position corresponding to position 239 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of R239F and R239Y.

In another embodiment, the variant comprises or consists of a substitution in the position corresponding to position 243 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of E243F, E243M, and E243W.

In another embodiment, the variant comprises or consists of a substitution in the position corresponding to position 245 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of G245A, G245C, G245E, G245K, G245M, G245N, G245Q, and G245R.

In another embodiment, the variant comprises or consists of a substitution in the position corresponding to position 257 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of S257A, S257C, S257D, S257E, S257G, S257H, S257K, S257P, and S257V.

In another embodiment, the variant comprises or consists of a substitution in the position corresponding to position 260 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of L260C, L260F, L260K, L260M, L260Q, L260Y, and L260T.

In another embodiment, the variant comprises or consists of a substitution in the position corresponding to position 267 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of T267D and T267E.

In another embodiment, the variant comprises or consists of a substitution in the position corresponding to position 270 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of N270A, N270C, and N270D.

In another embodiment, the variant comprises or consists of a substitution in the position corresponding to position 275 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of S275A, S275D, S275E, S275K, S275P, S275Q, S275T, and S275V.

In another embodiment, the variant comprises or consists of a substitution in the position corresponding to position 278 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of N278C, N278D, N278E, N278H, and N278W.

In another embodiment, the variant comprises or consists of a substitution in the position corresponding to position 282 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of N282C, N282F, and N282Y.

In another embodiment, the variant comprises or consists of a substitution in the position corresponding to position 283 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of D283G, D283S, and D283W.

In another embodiment, the variant comprises or consists of a substitution in the position corresponding to position 284 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of T284E and T284I.

In another embodiment, the variant comprises or consists of a substitution in the position corresponding to position 288 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of K288A and K288R.

In another embodiment, the variant comprises or consists of a substitution in the position corresponding to position 292 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of Q292E, Q292I, Q292M, Q292R, and Q292V.

In another embodiment, the variant comprises or consists of a substitution in the position corresponding to position 293 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is selected from the group of K293I, K293L, K293P, and K293R.

In another embodiment, the variant comprises or consists of a substitution in the position corresponding to position 295 of the polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 2 which has mannanase activity, and further the variant has improved stability compared to the mannanase of SEQ ID NO: 2. In one embodiment, the substitution is G295S.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for mannanase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

In one embodiment, the variant, polypeptide, or fragment thereof comprises at least two, such as at least three, such as at least four modifications in any two, three, four or more of the following positions: 8, 9, 11, 13, 18, 21, 34, 37, 45, 47, 65, 100, 101, 104, 107, 108, 110, 114, 115, 116, 132, 133, 142, 147, 152, 154, 164, 169, 173, 174, 176, 177, 180, 183, 185, 196, 199, 201, 202, 205, 206, 210, 215, 226, 229, 231, 239, 243, 245, 257, 260, 267, 270, 275, 278, 282, 283, 284, 288, 292, 293, and 295, wherein the variant, polypeptide, or fragments thereof have a half-life improvement factor of at least 1.0 when measured as improvement of detergent stability, protease stability, and/or thermostability at a pH of 8.0. Accordingly, the present invention also relates to a variant, polypeptide, or fragments thereof comprising at least two modification selected from the list of: 8+9, 8+11, 8+13, 8+18, 8+21, 8+34, 8+37, 8+45, 8+47, 8+65, 8+100, 8+101, 8+104, 8+107, 8+108, 8+110, 8+114, 8+115, 8+116, 8+132, 8+133, 8+142, 8+147, 8+152, 8+154, 8+164, 8+169, 8+173, 8+174, 8+176, 8+177, 8+180, 8+183, 8+185, 8+196, 8+199, 8+201, 8+202, 8+205, 8+206, 8+210, 8+215, 8+226, 8+229, 8+231, 8+239, 8+243, 8+245, 8+257, 8+260, 8+267, 8+270, 8+275, 8+278, 8+282, 8+283, 8+284, 8+288, 8+292, 8+293, 8+295, 9+11, 9+13, 9+18, 9+21, 9+34, 9+37, 9+45, 9+47, 9+65, 9+100, 9+101, 9+104, 9+107, 9+108, 9+110, 9+114, 9+115, 9+116, 9+132, 9+133, 9+142, 9+147, 9+152, 9+154, 9+164, 9+169, 9+173, 9+174, 9+176, 9+177, 9+180, 9+183, 9+185, 9+196, 9+199, 9+201, 9+202, 9+205, 9+206, 9+210, 9+215, 9+226, 9+229, 9+231, 9+239, 9+243, 9+245, 9+257, 9+260, 9+267, 9+270, 9+275, 9+278, 9+282, 9+283, 9+284, 9+288, 9+292, 9+293, 9+295, 11+13, 11+18, 11+21, 11+34, 11+37, 11+45, 11+47, 11+65, 11+100, 11+101, 11+104, 11+107, 11+108, 11+110, 11+114, 11+115, 11+116, 11+132, 11+133, 11+142, 11+147, 11+152, 11+154, 11+164, 11+169, 11+173, 11+174, 11+176, 11+177, 11+180, 11+183, 11+185, 11+196, 11+199, 11+201, 11+202, 11+205, 11+206, 11+210, 11+215, 11+226, 11+229, 11+231, 11+239, 11+243, 11+245, 11+257, 11+260, 11+267, 11+270, 11+275, 11+278, 11+282, 11+283, 11+284, 11+288, 11+292, 11+293, 11+295, 13+18, 13+21, 13+34, 13+37, 13+45, 13+47, 13+65, 13+100, 13+101, 13+104, 13+107, 13+108, 13+110, 13+114, 13+115, 13+116, 13+132, 13+133, 13+142, 13+147, 13+152, 13+154, 13+164, 13+169, 13+173, 13+174, 13+176, 13+177, 13+180, 13+183, 13+185, 13+196, 13+199, 13+201, 13+202, 13+205, 13+206, 13+210, 13+215, 13+226, 13+229, 13+231, 13+239, 13+243, 13+245, 13+257, 13+260, 13+267, 13+270, 13+275, 13+278, 13+282, 13+283, 13+284, 13+288, 13+292, 13+293, 13+295, 18+21, 18+34, 18+37, 18+45, 18+47, 18+65, 18+100, 18+101, 18+104, 18+107, 18+108, 18+110, 18+114, 18+115, 18+116, 18+132, 18+133, 18+142, 18+147, 18+152, 18+154, 18+164, 18+169, 18+173, 18+174, 18+176, 18+177, 18+180, 18+183, 18+185, 18+196, 18+199, 18+201, 18+202, 18+205, 18+206, 18+210, 18+215, 18+226, 18+229, 18+231, 18+239, 18+243, 18+245, 18+257, 18+260, 18+267, 18+270, 18+275, 18+278, 18+282, 18+283, 18+284, 18+288, 18+292, 18+293, 18+295, 21+34, 21+37, 21+45, 21+47, 21+65, 21+100, 21+101, 21+104, 21+107, 21+108, 21+110, 21+114, 21+115, 21+116, 21+132, 21+133, 21+142, 21+147, 21+152, 21+154, 21+164, 21+169, 21+173, 21+174, 21+176, 21+177, 21+180, 21+183, 21+185, 21+196, 21+199, 21+201, 21+202, 21+205, 21+206, 21+210, 21+215, 21+226, 21+229, 21+231, 21+239, 21+243, 21+245, 21+257, 21+260, 21+267, 21+270, 21+275, 21+278, 21+282, 21+283, 21+284, 21+288, 21+292, 21+293, 21+295, 34+37, 34+45, 34+47, 34+65, 34+100, 34+101, 34+104, 34+107, 34+108, 34+110, 34+114, 34+115, 34+116, 34+132, 34+133, 34+142, 34+147, 34+152, 34+154, 34+164, 34+169, 34+173, 34+174, 34+176, 34+177, 34+180, 34+183, 34+185, 34+196, 34+199, 34+201, 34+202, 34+205, 34+206, 34+210, 34+215, 34+226, 34+229, 34+231, 34+239, 34+243, 34+245, 34+257, 34+260, 34+267, 34+270, 34+275, 34+278, 34+282, 34+283, 34+284, 34+288, 34+292, 34+293, 34+295, 37+45, 37+47, 37+65, 37+100, 37+101, 37+104, 37+107, 37+108, 37+110, 37+114, 37+115, 37+116, 37+132, 37+133, 37+142, 37+147, 37+152, 37+154, 37+164, 37+169, 37+173, 37+174, 37+176, 37+177, 37+180, 37+183, 37+185, 37+196, 37+199, 37+201, 37+202, 37+205, 37+206, 37+210, 37+215, 37+226, 37+229, 37+231, 37+239, 37+243, 37+245, 37+257, 37+260, 37+267, 37+270, 37+275, 37+278, 37+282, 37+283, 37+284, 37+288, 37+292, 37+293, 37+295, 45+47, 45+65, 45+100, 45+101, 45+104, 45+107, 45+108, 45+110, 45+114, 45+115, 45+116, 45+132, 45+133, 45+142, 45+147, 45+152, 45+154, 45+164, 45+169, 45+173, 45+174, 45+176, 45+177, 45+180, 45+183, 45+185, 45+196, 45+199, 45+201, 45+202, 45+205, 45+206, 45+210, 45+215, 45+226, 45+229, 45+231, 45+239, 45+243, 45+245, 45+257, 45+260, 45+267, 45+270, 45+275, 45+278, 45+282, 45+283, 45+284, 45+288, 45+292, 45+293, 45+295, 47+65, 47+100, 47+101, 47+104, 47+107, 47+108, 47+110, 47+114, 47+115, 47+116, 47+132, 47+133, 47+142, 47+147, 47+152, 47+154, 47+164, 47+169, 47+173, 47+174, 47+176, 47+177, 47+180, 47+183, 47+185, 47+196, 47+199, 47+201, 47+202, 47+205, 47+206, 47+210, 47+215, 47+226, 47+229, 47+231, 47+239, 47+243, 47+245, 47+257, 47+260, 47+267, 47+270, 47+275, 47+278, 47+282, 47+283, 47+284, 47+288, 47+292, 47+293, 47+295, 65+100, 65+101, 65+104, 65+107, 65+108, 65+110, 65+114, 65+115, 65+116, 65+132, 65+133, 65+142, 65+147, 65+152, 65+154, 65+164, 65+169, 65+173, 65+174, 65+176, 65+177, 65+180, 65+183, 65+185, 65+196, 65+199, 65+201, 65+202, 65+205, 65+206, 65+210, 65+215, 65+226, 65+229, 65+231, 65+239, 65+243, 65+245, 65+257, 65+260, 65+267, 65+270, 65+275, 65+278, 65+282, 65+283, 65+284, 65+288, 65+292, 65+293, 65+295, 100+101, 100+104, 100+107, 100+108, 100+110, 100+114, 100+115, 100+116, 100+132, 100+133, 100+142, 100+147, 100+152, 100+154, 100+164, 100+169, 100+173, 100+174, 100+176, 100+177, 100+180, 100+183, 100+185, 100+196, 100+199, 100+201, 100+202, 100+205, 100+206, 100+210, 100+215, 100+226, 100+229, 100+231, 100+239, 100+243, 100+245, 100+257, 100+260, 100+267, 100+270, 100+275, 100+278, 100+282, 100+283, 100+284, 100+288, 100+292, 100+293, 100+295, 101+104, 101+107, 101+108, 101+110, 101+114, 101+115, 101+116, 101+132, 101+133, 101+142, 101+147, 101+152, 101+154, 101+164, 101+169, 101+173, 101+174, 101+176, 101+177, 101+180, 101+183, 101+185, 101+196, 101+199, 101+201, 101+202, 101+205, 101+206, 101+210, 101+215, 101+226, 101+229, 101+231, 101+239, 101+243, 101+245, 101+257, 101+260, 101+267, 101+270, 101+275, 101+278, 101+282, 101+283, 101+284, 101+288, 101+292, 101+293, 101+295, 104+107, 104+108, 104+110, 104+114, 104+115, 104+116, 104+132, 104+133, 104+142, 104+147, 104+152, 104+154, 104+164, 104+169, 104+173, 104+174, 104+176, 104+177, 104+180, 104+183, 104+185, 104+196, 104+199, 104+201, 104+202, 104+205, 104+206, 104+210, 104+215, 104+226, 104+229, 104+231, 104+239, 104+243, 104+245, 104+257, 104+260, 104+267, 104+270, 104+275, 104+278, 104+282, 104+283, 104+284, 104+288, 104+292, 104+293, 104+295, 107+108, 107+110, 107+114, 107+115, 107+116, 107+132, 107+133, 107+142, 107+147, 107+152, 107+154, 107+164, 107+169, 107+173, 107+174, 107+176, 107+177, 107+180, 107+183, 107+185, 107+196, 107+199, 107+201, 107+202, 107+205, 107+206, 107+210, 107+215, 107+226, 107+229, 107+231, 107+239, 107+243, 107+245, 107+257, 107+260, 107+267, 107+270, 107+275, 107+278, 107+282, 107+283, 107+284, 107+288, 107+292, 107+293, 107+295, 108+110, 108+114, 108+115, 108+116, 108+132, 108+133, 108+142, 108+147, 108+152, 108+154, 108+164, 108+169, 108+173, 108+174, 108+176, 108+177, 108+180, 108+183, 108+185, 108+196, 108+199, 108+201, 108+202, 108+205, 108+206, 108+210, 108+215, 108+226, 108+229, 108+231, 108+239, 108+243, 108+245, 108+257, 108+260, 108+267, 108+270, 108+275, 108+278, 108+282, 108+283, 108+284, 108+288, 108+292, 108+293, 108+295, 110+114, 110+115, 110+116, 110+132, 110+133, 110+142, 110+147, 110+152, 110+154, 110+164, 110+169, 110+173, 110+174, 110+176, 110+177, 110+180, 110+183, 110+185, 110+196, 110+199, 110+201, 110+202, 110+205, 110+206, 110+210, 110+215, 110+226, 110+229, 110+231, 110+239, 110+

243, 110+245, 110+257, 110+260, 110+267, 110+270, 110+275, 110+278, 110+282, 110+283, 110+284, 110+288, 110+292, 110+293, 110+295, 114+115, 114+116, 114+132, 114+133, 114+142, 114+147, 114+152, 114+154, 114+164, 114+169, 114+173, 114+174, 114+176, 114+177, 114+180, 114+183, 114+185, 114+196, 114+199, 114+201, 114+202, 114+205, 114+206, 114+210, 114+215, 114+226, 114+229, 114+231, 114+239, 114+243, 114+245, 114+257, 114+260, 114+267, 114+270, 114+275, 114+278, 114+282, 114+283, 114+284, 114+288, 114+292, 114+293, 114+295, 115+116, 115+132, 115+133, 115+142, 115+147, 115+152, 115+154, 115+164, 115+169, 115+173, 115+174, 115+176, 115+177, 115+180, 115+183, 115+185, 115+196, 115+199, 115+201, 115+202, 115+205, 115+206, 115+210, 115+215, 115+226, 115+229, 115+231, 115+239, 115+243, 115+245, 115+257, 115+260, 115+267, 115+270, 115+275, 115+278, 115+282, 115+283, 115+284, 115+288, 115+292, 115+293, 115+295, 116+132, 116+133, 116+142, 116+147, 116+152, 116+154, 116+164, 116+169, 116+173, 116+174, 116+176, 116+177, 116+180, 116+183, 116+185, 116+196, 116+199, 116+201, 116+202, 116+205, 116+206, 116+210, 116+215, 116+226, 116+229, 116+231, 116+239, 116+243, 116+245, 116+257, 116+260, 116+267, 116+270, 116+275, 116+278, 116+282, 116+283, 116+284, 116+288, 116+292, 116+295, 132+133, 132+142, 132+147, 132+152, 132+154, 132+164, 132+169, 132+173, 132+174, 132+176, 132+177, 132+180, 132+183, 132+185, 132+196, 132+199, 132+201, 132+202, 132+205, 132+206, 132+210, 132+215, 132+226, 132+229, 132+231, 132+239, 132+243, 132+245, 132+257, 132+260, 132+267, 132+270, 132+275, 132+278, 132+282, 132+283, 132+284, 132+288, 132+292, 132+293, 132+295, 133+142, 133+147, 133+152, 133+154, 133+164, 133+169, 133+173, 133+174, 133+176, 133+177, 133+180, 133+183, 133+185, 133+196, 133+199, 133+201, 133+202, 133+205, 133+206, 133+210, 133+215, 133+226, 133+229, 133+231, 133+239, 133+243, 133+245, 133+257, 133+260, 133+267, 133+270, 133+275, 133+278, 133+282, 133+283, 133+284, 133+288, 133+292, 133+293, 133+295, 142+147, 142+152, 142+154, 142+164, 142+169, 142+173, 142+174, 142+176, 142+177, 142+180, 142+183, 142+185, 142+196, 142+199, 142+201, 142+202, 142+205, 142+206, 142+210, 142+215, 142+226, 142+229, 142+231, 142+239, 142+243, 142+245, 142+257, 142+260, 142+267, 142+270, 142+275, 142+278, 142+282, 142+283, 142+284, 142+288, 142+292, 142+293, 142+295, 147+152, 147+154, 147+164, 147+169, 147+173, 147+174, 147+176, 147+177, 147+180, 147+183, 147+185, 147+196, 147+199, 147+201, 147+202, 147+205, 147+206, 147+210, 147+215, 147+226, 147+229, 147+231, 147+239, 147+243, 147+245, 147+257, 147+260, 147+267, 147+270, 147+275, 147+278, 147+282, 147+283, 147+284, 147+288, 147+292, 147+293, 147+295, 152+154, 152+164, 152+169, 152+173, 152+174, 152+176, 152+177, 152+180, 152+183, 152+185, 152+196, 152+199, 152+201, 152+202, 152+205, 152+206, 152+210, 152+215, 152+226, 152+229, 152+231, 152+239, 152+243, 152+245, 152+257, 152+260, 152+267, 152+270, 152+275, 152+278, 152+282, 152+283, 152+284, 152+288, 152+292, 152+293, 152+295, 154+164, 154+169, 154+173, 154+174, 154+176, 154+177, 154+180, 154+183, 154+185, 154+196, 154+199, 154+201, 154+202, 154+205, 154+206, 154+210, 154+215, 154+226, 154+229, 154+231, 154+239, 154+243, 154+245, 154+257, 154+260, 154+267, 154+270, 154+275, 154+278, 154+282, 154+283, 154+284, 154+288, 154+292, 154+293, 154+295, 164+169, 164+173, 164+174, 164+176, 164+177, 164+180, 164+183, 164+185, 164+196, 164+199, 164+201, 164+202, 164+205, 164+206, 164+210, 164+215, 164+226, 164+229, 164+231, 164+239, 164+243, 164+245, 164+257, 164+260, 164+267, 164+270, 164+275, 164+278, 164+282, 164+283, 164+284, 164+288, 164+292, 164+293, 164+295, 169+173, 169+174, 169+176, 169+177, 169+180, 169+183, 169+185, 169+196, 169+199, 169+201, 169+202, 169+205, 169+206, 169+210, 169+215, 169+226, 169+229, 169+231, 169+239, 169+243, 169+245, 169+257, 169+260, 169+267, 169+270, 169+275, 169+278, 169+282, 169+283, 169+284, 169+288, 169+292, 169+293, 169+295, 173+174, 173+176, 173+177, 173+180, 173+183, 173+185, 173+196, 173+199, 173+201, 173+202, 173+205, 173+206, 173+210, 173+215, 173+226, 173+229, 173+231, 173+239, 173+243, 173+245, 173+257, 173+260, 173+267, 173+270, 173+275, 173+278, 173+282, 173+283, 173+284, 173+288, 173+292, 173+293, 173+295, 174+176, 174+177, 174+180, 174+183, 174+185, 174+196, 174+199, 174+201, 174+202, 174+205, 174+206, 174+210, 174+215, 174+226, 174+229, 174+231, 174+239, 174+243, 174+245, 174+257, 174+260, 174+267, 174+270, 174+275, 174+278, 174+282, 174+283, 174+284, 174+288, 174+292, 174+293, 174+295, 176+177, 176+180, 176+183, 176+185, 176+196, 176+199, 176+201, 176+202, 176+205, 176+206, 176+210, 176+215, 176+226, 176+229, 176+231, 176+239, 176+243, 176+245, 176+257, 176+260, 176+267, 176+270, 176+275, 176+278, 176+282, 176+283, 176+284, 176+288, 176+292, 176+293, 176+295, 177+180, 177+183, 177+185, 177+196, 177+199, 177+201, 177+202, 177+205, 177+206, 177+210, 177+215, 177+226, 177+229, 177+231, 177+239, 177+243, 177+245, 177+257, 177+260, 177+267, 177+270, 177+275, 177+278, 177+282, 177+283, 177+284, 177+288, 177+292, 177+293, 177+295, 180+183, 180+185, 180+196, 180+199, 180+201, 180+202, 180+205, 180+206, 180+210, 180+215, 180+226, 180+229, 180+231, 180+239, 180+243, 180+245, 180+257, 180+260, 180+267, 180+270, 180+275, 180+278, 180+282, 180+283, 180+284, 180+288, 180+292, 180+293, 180+295, 183+185, 183+196, 183+199, 183+201, 183+202, 183+205, 183+206, 183+210, 183+215, 183+226, 183+229, 183+231, 183+239, 183+243, 183+245, 183+257, 183+260, 183+267, 183+270, 183+275, 183+278, 183+282, 183+283, 183+284, 183+288, 183+292, 183+293, 183+295, 185+196, 185+199, 185+201, 185+202, 185+205, 185+206, 185+210, 185+215, 185+226, 185+229, 185+231, 185+239, 185+243, 185+245, 185+257, 185+260, 185+267, 185+270, 185+275, 185+278, 185+282, 185+283, 185+284, 185+288, 185+292, 185+293, 185+295, 196+199, 196+201, 196+202, 196+205, 196+206, 196+210, 196+215, 196+226, 196+229, 196+231, 196+239, 196+243, 196+245, 196+257, 196+260, 196+267, 196+270, 196+275, 196+278, 196+282, 196+283, 196+284, 196+288, 196+292, 196+293, 196+295, 199+201, 199+202, 199+205, 199+206, 199+210, 199+215, 199+226, 199+229, 199+231, 199+239, 199+243, 199+245, 199+257, 199+260, 199+267, 199+270, 199+275, 199+278, 199+282, 199+283, 199+284, 199+288, 199+292, 199+293, 199+295, 201+202, 201+205, 201+206, 201+210, 201+215, 201+226, 201+229, 201+231, 201+239, 201+243, 201+245, 201+257, 201+260, 201+267, 201+270, 201+275, 201+278, 201+282, 201+283, 201+284, 201+288, 201+292, 201+293, 201+295, 202+205, 202+206, 202+210, 202+215, 202+226, 202+229, 202+231, 202+239, 202+243, 202+245, 202+257, 202+260, 202+267, 202+270, 202+275, 202+278, 202+282, 202+283, 202+284, 202+288, 202+292, 202+293, 202+295, 205+206, 205+210, 205+215, 205+226, 205+229, 205+231, 205+239, 205+243, 205+245, 205+257, 205+260, 205+267, 205+270, 205+275, 205+278, 205+282, 205+283, 205+284, 205+288, 205+292, 205+293, 205+295, 206+210, 206+215, 206+226, 206+229, 206+231, 206+239, 206+243, 206+245, 206+257, 206+260, 206+267, 206+270, 206+275, 206+278, 206+282, 206+283, 206+284, 206+288, 206+292, 206+293, 206+295, 210+215, 210+226, 210+229, 210+231, 210+239, 210+243, 210+245, 210+257, 210+260, 210+

267, 210+270, 210+275, 210+278, 210+282, 210+283, 210+ 284, 210+288, 210+292, 210+293, 210+295, 215+226, 215+ 229, 215+231, 215+239, 215+243, 215+245, 215+257, 215+ 260, 215+267, 215+270, 215+275, 215+278, 215+282, 215+ 283, 215+284, 215+288, 215+292, 215+293, 215+295, 226+ 229, 226+231, 226+239, 226+243, 226+245, 226+257, 226+ 260, 226+267, 226+270, 226+275, 226+278, 226+282, 226+ 283, 226+284, 226+288, 226+292, 226+293, 226+295, 229+ 231, 229+239, 229+243, 229+245, 229+257, 229+260, 229+ 267, 229+270, 229+275, 229+278, 229+282, 229+283, 229+ 284, 229+288, 229+292, 229+293, 229+295, 231+239, 231+ 243, 231+245, 231+257, 231+260, 231+267, 231+270, 231+ 275, 231+278, 231+282, 231+283, 231+284, 231+288, 231+ 292, 231+293, 231+295, 239+243, 239+245, 239+257, 239+ 260, 239+267, 239+270, 239+275, 239+278, 239+282, 239+ 283, 239+284, 239+288, 239+292, 239+293, 239+295, 243+ 245, 243+257, 243+260, 243+267, 243+270, 243+275, 243+ 278, 243+282, 243+283, 243+284, 243+288, 243+292, 243+ 293, 243+295, 245+257, 245+260, 245+267, 245+270, 245+ 275, 245+278, 245+282, 245+283, 245+284, 245+288, 245+ 292, 245+293, 245+295, 257+260, 257+267, 257+270, 257+ 275, 257+278, 257+282, 257+283, 257+284, 257+288, 257+ 292, 257+293, 257+295, 260+267, 260+270, 260+275, 260+ 278, 260+282, 260+283, 260+284, 260+288, 260+292, 260+ 293, 260+295, 267+270, 267+275, 267+278, 267+282, 267+ 283, 267+284, 267+288, 267+292, 267+293, 267+295, 270+ 275, 270+278, 270+282, 270+283, 270+284, 270+288, 270+ 292, 270+293, 270+295, 275+278, 275+282, 275+283, 275+ 284, 275+288, 275+292, 275+293, 275+295, 278+282, 278+ 283, 278+284, 278+288, 278+292, 278+293, 278+295, 282+ 283, 282+284, 282+288, 282+292, 282+293, 282+295, 283+ 284, 283+288, 283+292, 283+293, 283+295, 284+288, 284+ 292, 284+293, 284+295, 288+292, 288+293, 288+295, 292+ 293, 292+295, and 293+295.

In one embodiment, the variant, polypeptide, or fragments thereof comprises at least two, such as at least three, such as at least four substitutions selected from the group of S8A, S8D, S8E, S8I, S8K, S8L, S8M, S8R, S8T, G9L, G9Q, G9R, G9S, G9V, G9W, G9Y, K11A, K11M, K11Q, K11R, K11S, K11V, Y13F, Y13I, Y13M, K18A, K18F, K18L, K18Q, K18R, K18S, V21I, V21M, N34C, N34E, N37C, N37D, N37H, N37Y, N37G, N37Q, K45A, K45C, K45D, K45E, K45G, K45H, K45M, K45N, K45Q, K45R, K45S, K45T, G47A, G47D, G47L, G47Q, G47R, G47S, D65P, D100G, D100K, D100L, A101C, A101E, A101L, A101N, A101M, A101Q, N104I, N104L, N104T, N104V, N104Y, N104C, N104M, N104Q, N104W, I107C, I107V, S108A, S108D, S108E, S108F, S108G, S108V, S108W, S108Y, K110A, K110G, K110H, K110N, K110Q, K110C, K110L, K110M, K110S, K110T, I114A, I114C, I114F, I114G, I114H, I114L, I114M, I114N, I114Q, I114R, I114T, I114V, I114W, I114Y, G115C, G115D, G115F, G115H, G115M, G115R, G115W, K116L, K116M, K116V, W132O, W132E, W132M, W132Q, W132Y, N133A, N133C, N133D, N133F, N133G, N133K, N133L, N133M, N133R, N133S, N133T, N133W, K142F, K142L, K142C, K142E, K142I, K142M, K142Q, K142R, K142V, K142W, K142Y, K147H, K147I, K147S, G152C, G152E, G152M, G152N, G152Q, G152R, G152S, K154A, K154D, K154E, K154F, K154G, K154H, K154L, K154M, K154T, K154W, W164D, W164F, W164M, W164Q, W164S, W164Y, Q169A, Q169M, D173Q, D173E, Y174F, Q176A, Q176O, Q176E, Q176G, Q176H, Q176K, Q176L, Q176M, Q176R, Q176P, S177A, S177C, S177D, S177E, S177H, S177I, S177L, S177Q, S177R, S177T, S177V, A180E, A180Q, S183A, S183D, S183E, S183G, S183I, S183P, S183R, S183V, S183W, K185G, K185S, K185T, K185V, K185W, K185Y, Y196I, Y196V, K199A, A201E, A202C, A202K, A202M, A202P, A202R, A202W, K205A, K205C, K205D, K205L, K205N, K205S, A206L, A206M, A206F, A206T, N210A, N210G, N210S, G215M, Y226C, Y226G, Y226K, Y226N, Y226Q, Y226R, Y226S, Y226T, Y226W, N229C, D231P, D231T, R239F, R239Y, E243F, E243M, E243W, G245A, G245C, G245E, G245K, G245M, G245N, G245Q, G245R, S257A, S257C, S257D, S257E, S257G, S257H, S257K, S257P, S257V, L260C, L260F, L260K, L260M, L260Q, L260Y, L260T, T267D, T267E, N270A, N270C, N270D, S275A, S275D, S275E, S275K, S275P, S275Q, S275T, S275V, N278C, N278D, N278E, N278H, N278W, N282C, N282F, N282Y, D283G, D283S, D283W, T284E, T284I, K288A, K288R, Q292E, Q292I, Q292M, Q292R, Q292V, K293I, K293L, K293P, K293R, and G295S, wherein the variant, polypeptide, or fragments thereof have a half-life improvement factor of at least 1.0 when measured as improvement of detergent stability, protease stability, and/or thermostability at a pH of 8.0.

In an embodiment, the variant, polypeptide, or fragment thereof has sequence identity of at least 59%, e.g. at least 60%, e.g., at least 62, at least 63%, at least 64%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent mannanase.

In another embodiment, the variant, polypeptide, or fragment thereof has at least 59%, e.g. at least 60%, e.g., at least 62, at least 63%, at least 64%, at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1, the polypeptide of SEQ ID NO: 2, the polypeptide of SEQ ID NO: 3, or the polypeptide of SEQ ID NO: 4.

In one particular embodiment, the variant, polypeptide, or fragment thereof has as at least 59%, e.g. at least 60%, e.g., at least 62, at least 63%, at least 64%, at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1.

In one particular embodiment, the variant, polypeptide, or fragment thereof has as at least 59%, e.g. at least 60%, e.g., at least 62, at least 63%, at least 64%, at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 2.

In another particular embodiment, the variant, polypeptide, or fragment thereof has as at least 59%, e.g. at least 60%, e.g., at least 62, at least 63%, at least 64%, at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3.

In another particular embodiment, the variant, polypeptide, or fragment thereof has as at least 59%, e.g. at least 60%, e.g., at least 62, at least 63%, at least 64%, at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 4.

In a particular embodiment, the parent polypeptide comprises or consists of the mature polypeptide of SEQ ID NO: 1.

In a further particular embodiment, the parent polypeptide consists of the mature polypeptide of SEQ ID NO: 1.

In one embodiment, the parent polypeptide is a fragment of the mature polypeptide of SEQ ID NO: 1, wherein the fragment has mannanase activity.

In one embodiment, the variant, polypeptide, or fragment thereof has at least 60%, e.g., at least 65%, at least 70%, at least 75%, at least 80%, at least 85%, at least 90%, at least 95% identity, at least 96%, at least 97%, at least 98%, or at least 99%, but less than 100%, sequence identity to the amino acid sequence of the parent polypeptide.

The variant or polypeptide may be a fragment which has mannanase activity. Accordingly, the present invention also relates to fragments of variants or polypeptides having mannanase activity. Such fragments may consist of 250 to 300, e.g., 260 to 300, 270 to 300, 285 to 300 amino acids. Thus, in one embodiment, the fragment consists of 250 to 300, e.g., 260 to 300, 270 to 300, 285 to 300 amino acids.

The variant, polypeptide, or fragment thereof according to the invention have an improved property relative to the parent polypeptide, wherein the improved property is selected from the group consisting of catalytic efficiency, catalytic rate, chemical stability, oxidation stability, in-detergent stability, pH activity, pH stability, specific activity, stability under storage conditions, substrate binding, substrate cleavage, substrate specificity, substrate stability, surface properties, thermal activity, and thermostability. Thus, in one embodiment, the variant, polypeptide, or fragment thereof have an improved property relative to the parent polypeptide, wherein the improved property is selected from the group consisting of catalytic efficiency, catalytic rate, chemical stability, oxidation stability, in-detergent stability, pH activity, pH stability, specific activity, stability under storage conditions, substrate binding, substrate cleavage, substrate specificity, substrate stability, surface properties, thermal activity, and thermostability.

In particular embodiments, the variant, polypeptide, or fragment thereof has an improved detergent stability or thermostability, which may be determined as described in the Examples. In particular, the stability may be determined at a pH of 8.0. Thus, in one embodiment, the variant of the present invention has an improved stability when measured at pH 8.0.

In another particular embodiment, the variant, polypeptide, or fragment thereof has an improved protease stability. Improved protease stability according to the present invention means that the variant, polypeptide or fragment thereof is more resistant to cleavage of a proteases than the parent polypeptide. Thus, when the variant, polypeptide, or fragment thereof is incubated or simply combined in a composition of any kind with a protease, the variant, polypeptide or fragment thereof will maintain its mannanase activity regardless of the protease. In the context of "maintaining the mannanase activity" as used herein, means that the mannanase activity is at least 50% of the initial activity measured over a period of time. Thus, variants, polypeptides, or fragments thereof according to the invention will have maintained a higher percentage of activity over a period of time compared to the parent polypeptide. This is also defined elsewhere herein.

Thus, in one embodiment, the mannanase activity is in the presence of a protease and/or a detergent component and/or detergent composition.

The protease may be any protease, e.g. a wild-type protease or a variant protease. Thus, in one embodiment, the protease is a protease having at least 60% sequence identity to the polypeptide of SEQ ID NO: 5.

In one embodiment, the protease is a variant of SEQ ID NO: 5 which comprises one or more of the following modifications S9E, N42R, N74D, V199I, Q200L, Y203W, S253D, N255W, and L256E, wherein numbering is according to SEQ ID NO: 5. In one particular embodiment, the protease variant comprises all of the modifications S9E, N42R, N74D, V199I, Q200L, Y203W, S253D, N255W, and L256E Parent Mannanases The parent mannanase may be (a) a polypeptide having at least 65% sequence identity to the mature polypeptide of SEQ ID NO: 1; (b) a polypeptide encoded by a polynucleotide that hybridizes under low stringency conditions with (i) the mature polypeptide coding sequence of SEQ ID NO: 3, (ii) the full-length complement of (i); or (c) a polypeptide encoded by a polynucleotide having at least 65% sequence identity to the mature polypeptide coding sequence of SEQ ID NO: 3.

In an aspect, the parent mannanase has a sequence identity to the mature polypeptide of SEQ ID NO: 1 of at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which has mannanase activity. In one aspect, the amino acid sequence of the parent mannanase differs by up to 20 amino acids, e.g., 1, 2, 3, 4, 5, 6, 7, 8, 9, 10, 11, 12, 13, 14, 15, 16, 17, 18, 19, or 20 from the mature polypeptide of SEQ ID NO: 1.

In an aspect, the parent mannanase has a sequence identity to the polypeptide of SEQ ID NO: 2 of at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which has mannanase activity. In one aspect, the amino acid sequence of the parent mannanase differs by up to 20 amino acids, e.g., 1, 2, 3, 4, 5, 6, 7, 8, 9, 10, 11, 12, 13, 14, 15, 16, 17, 18, 19, or 20 from the mature polypeptide of SEQ ID NO: 2.

In another aspect, the parent comprises or consists of the amino acid sequence of SEQ ID NO: 2. In another aspect, the parent comprises or consists of the mature polypeptide of SEQ ID NO: 1.

In another aspect, the parent is a fragment of the polypeptide of SEQ ID NO: 2 containing at least 250 amino acid residues, e.g., at least 270 and at least 290 amino acid residues.

In another embodiment, the parent is an allelic variant of the polypeptide of SEQ ID NO: 2.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 3, or (ii) the full-length complement of (i) or (ii) (Sambrook et al., 1989, *Molecular Cloning, A Laboratory Manual*, 2d edition, Cold Spring Harbor, N.Y.).

The polynucleotide of SEQ ID NO: 3 or a subsequence thereof, as well as the polypeptide of SEQ ID NO: 2 or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^3H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 3; (ii) the mature polypeptide coding sequence of SEQ ID NO: 3; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 3. In another aspect, the nucleic acid probe is a polynucleotide that encodes the polypeptide of SEQ ID NO: 1; the mature polypeptide thereof; or a fragment thereof. In another aspect, the nucleic acid probe is SEQ ID NO: 3.

In another embodiment, the parent is encoded by a polynucleotide having a sequence identity to the mature polypeptide coding sequence of SEQ ID NO: 3 of at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial mannanase. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* mannanase, or a Gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* mannanase.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* mannanase.

In another aspect, the parent is a *Streptococcus equisimilis, Streptococcus pyogenes, Streptococcus uberis*, or *Streptococcus equi* subsp. *Zooepidemicus* mannanase.

In another aspect, the parent is a *Streptomyces achromogenes, Streptomyces avermitilis, Streptomyces coelicolor, Streptomyces griseus*, or *Streptomyces lividans* mannanase.

In another aspect, the parent is a *Bacillus bogoriensis* mannanase, e.g., the mannanase of SEQ ID NO: 1 or the mature polypeptide thereof.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having mannanase activity, comprising: (a) introducing into a parent mannanase a modification, such as a deletion or substitution at one position corresponding to positions 1, 2, 3, 4, 5, 6, 8, 9, 10, 11, 13, 14, 15, 16, 17, 18, 19, 21, 23, 30, 32, 33, 34, 35, 37, 38, 39, 41, 44, 45, 47, 57, 59, 60, 62, 63, 65, 66, 67, 68, 70, 71, 74, 77, 78, 79, 80, 81, 82, 83, 93, 95, 96, 97, 98, 100, 104, 107, 108, 110, 111, 114, 115, 116, 118, 119, 131, 132, 133, 135, 136, 139, 142, 143, 146, 147, 150, 152, 154, 164, 167, 169, 172, 173, 174, 175, 176, 177, 180, 181, 183, 184, 185, 196, 199, 200, 201, 202, 203, 205, 206, 210, 212, 213, 214, 215, 226, 228, 229, 230, 234, 235, 241, 242, 243, 244, 245, 250, 254, 257, 258, 259, 260, 261, 262, 266, 267, 268, 270, 271, 272, 273, 276, 279, 280, 283, 285, 286, 288, 289, 290, 292, 293, 294, 295, and 296 of the mature polypeptide of SEQ ID NO: 1, wherein the variant has mannanase activity; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention. Thus, in one aspect, the present invention relates to a polynucleotide encoding a variant comprising a modification at one position corresponding to a position selected from the positions 1, 2, 3, 4, 5, 6, 8, 9, 10, 11, 13, 14, 15, 16, 17, 18, 19, 21, 23, 30, 32, 33, 34, 35, 37, 38, 39, 41, 44, 45, 47, 57, 59, 60, 62, 63, 65, 66, 67, 68, 70, 71, 74, 77, 78, 79, 80, 81, 82, 83, 93, 95, 96, 97, 98, 100, 104, 107, 108, 110, 111, 114, 115, 116, 118, 119, 131, 132, 133, 135, 136, 139, 142, 143, 146, 147, 150, 152, 154, 164, 167, 169, 172, 173, 174, 175, 176, 177, 180, 181, 183, 184, 185, 196, 199, 200, 201, 202, 203, 205, 206, 210, 212, 213, 214, 215, 226, 228, 229, 230, 234, 235, 241, 242, 243, 244, 245, 250, 254, 257, 258, 259, 260, 261, 262, 266, 267, 268, 270, 271, 272, 273, 276, 279, 280, 283, 285, 286, 288, 289, 290, 292, 293, 294, 295, and 296 of the polypeptide of SEQ ID NO: 2, wherein each modification is independently a substitution or a deletion, wherein said variant has at least 65%, e.g., at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences. Thus, in one aspect, the present invention relates to a polynucleotide encoding a variant comprising a modification at one position corresponding to a position selected from the positions 1, 2, 3, 4, 5, 6, 8, 9, 10, 11, 13, 14, 15, 16, 17, 18, 19, 21, 23, 30, 32, 33, 34, 35, 37, 38, 39, 41, 44, 45, 47, 57, 59, 60, 62, 63, 65, 66, 67, 68, 70, 71, 74, 77, 78, 79, 80, 81, 82, 83, 93, 95, 96, 97, 98, 100, 104, 107, 108, 110, 111, 114, 115, 116, 118, 119, 131, 132, 133, 135, 136, 139, 142, 143, 146, 147, 150, 152, 154, 164, 167, 169, 172, 173, 174, 175, 176, 177, 180, 181, 183, 184, 185, 196, 199, 200, 201, 202, 203, 205, 206, 210, 212, 213, 214, 215, 226, 228, 229, 230, 234, 235, 241, 242, 243, 244, 245, 250, 254, 257, 258, 259, 260, 261, 262, 266, 267, 268, 270, 271, 272, 273, 276, 279, 280, 283, 285, 286, 288, 289, 290, 292, 293, 294, 295, and 296, of the polypeptide of SEQ ID NO: 2, wherein each modification is independently a substitution or a deletion, wherein said variant has at least 65%, e.g., at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2, operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, Journal of Bacteriology 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCI B 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. Thus, in one aspect, the present invention relates to recombinant expression vectors comprising a polynucleotide encoding a variant comprising a modification at one position corresponding to a position selected from the positions 1, 2, 3, 4, 5, 6, 8, 9, 10, 11, 13, 14, 15, 16, 17, 18, 19, 21, 23, 30, 32, 33, 34, 35, 37, 38, 39, 41, 44, 45, 47, 57, 59, 60, 62, 63, 65, 66, 67, 68, 70, 71, 74, 77, 78, 79, 80, 81, 82, 83, 93, 95, 96, 97, 98, 100, 104, 107, 108, 110, 111, 114, 115, 116, 118, 119, 131, 132, 133, 135, 136, 139, 142, 143, 146, 147, 150, 152, 154, 164, 167, 169, 172, 173, 174, 175, 176, 177, 180, 181, 183, 184, 185, 196, 199, 200, 201, 202, 203, 205, 206, 210, 212, 213, 214, 215, 226, 228, 229, 230, 234, 235, 241, 242, 243, 244, 245, 250, 254, 257, 258, 259, 260, 261, 262, 266, 267, 268, 270, 271, 272, 273, 276, 279, 280, 283, 285, 286, 288, 289, 290, 292, 293, 294, 295, and 296, of the polypeptide of SEQ ID NO: 2, wherein each modification is independently a substitution or a deletion, wherein said variant has at least 65%, e.g., at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2, a promoter, and transcriptional and translational stop signals.

The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. Thus, in one aspect, the present invention relates to recombinant host cells, comprising a polynucleotide encoding a variant comprising a modification at one position corresponding to a position selected from the positions 1, 2, 3, 4, 5, 6, 8, 9, 10, 11, 13, 14, 15, 16, 17, 18, 19, 21, 23, 30, 32, 33, 34, 35, 37, 38, 39, 41, 44, 45, 47, 57, 59, 60, 62, 63, 65, 66, 67, 68, 70, 71, 74, 77, 78, 79, 80, 81, 82, 83, 93, 95, 96, 97, 98, 100, 104, 107, 108, 110, 111, 114, 115, 116, 118, 119, 131, 132, 133, 135, 136, 139, 142, 143, 146, 147, 150, 152, 154, 164, 167, 169, 172, 173, 174, 175, 176, 177, 180, 181, 183, 184, 185, 196, 199, 200, 201, 202, 203, 205, 206, 210, 212, 213, 214, 215, 226, 228, 229, 230, 234, 235, 241, 242, 243, 244, 245, 250, 254, 257, 258, 259, 260, 261, 262, 266, 267, 268, 270, 271, 272, 273, 276, 279, 280, 283, 285, 286, 288, 289, 290, 292, 293, 294, 295, and 296, of the polypeptide of SEQ ID NO: 2, wherein each modification is independently a substitution or a deletion, wherein said variant has at least 65%, e.g., at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2, operably linked to one or more control sequences that direct the production of a variant comprising a modification at one position corresponding to a position selected from the positions 1, 2, 3, 4, 5, 6, 8, 9, 10, 11, 13, 14, 15, 16, 17, 18, 19, 21, 23, 30, 32, 33, 34, 35, 37, 38, 39, 41, 44, 45, 47, 57, 59, 60, 62, 63, 65, 66, 67, 68, 70, 71, 74, 77, 78, 79, 80, 81, 82, 83, 93, 95, 96, 97, 98, 100, 104, 107, 108, 110, 111, 114, 115, 116, 118, 119, 131, 132, 133, 135, 136, 139, 142, 143, 146, 147, 150, 152, 154, 164, 167, 169, 172, 173, 174, 175, 176, 177, 180, 181, 183, 184, 185, 196, 199, 200, 201, 202, 203, 205, 206, 210, 212, 213, 214, 215, 226, 228, 229, 230, 234, 235, 241, 242, 243, 244, 245, 250, 254, 257, 258, 259, 260, 261, 262, 266, 267, 268, 270, 271, 272, 273, 276, 279, 280, 283, 285, 286, 288, 289, 290, 292, 293, 294, 295, and 296, of the polypeptide of SEQ ID NO: 2, wherein each modification is independently a substitution or a deletion, wherein said variant has at least 65%, e.g., at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2.

A construct or vector comprising a polynucleotide is introduced into a host cell so that the construct or vector is maintained as a chromosomal integrant or as a self-replicating extrachromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980).

Fungal cells may be transformed by a process involving protoplast formation, transformation of the protoplasts, and regeneration of the cell wall in a manner known per se. Suitable procedures for transformation of Aspergillus and Trichoderma host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming Fusarium species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

Methods of Production

The present invention also relates to methods of producing a variant, comprising: (a) cultivating a host cell of the present invention under conditions suitable for expression of the variant; and (b) recovering the variant. Thus, in one aspect, the present invention relates to methods of producing a variant, comprising the steps of (a) cultivating a host cell comprising a polynucleotide encoding a variant comprising a modification at one position corresponding to a position selected from the positions 1, 2, 3, 4, 5, 6, 8, 9, 10, 11, 13, 14, 15, 16, 17, 18, 19, 21, 23, 30, 32, 33, 34, 35, 37, 38, 39, 41, 44, 45, 47, 57, 59, 60, 62, 63, 65, 66, 67, 68, 70, 71, 74, 77, 78, 79, 80, 81, 82, 83, 93, 95, 96, 97, 98, 100, 104, 107, 108, 110, 111, 114, 115, 116, 118, 119, 131, 132, 133, 135, 136, 139, 142, 143, 146, 147, 150, 152, 154, 164, 167, 169, 172, 173, 174, 175, 176, 177, 180, 181, 183, 184, 185, 196, 199, 200, 201, 202, 203, 205, 206, 210, 212, 213, 214, 215, 226, 228, 229, 230, 234, 235, 241, 242, 243, 244, 245, 250, 254, 257, 258, 259, 260, 261, 262, 266, 267, 268, 270, 271, 272, 273, 276, 279, 280, 283, 285, 286, 288, 289, 290, 292, 293, 294, 295, and 296, of the polypeptide of SEQ ID NO: 2, wherein each modification is independently a substitution or a deletion, wherein said variant has at least 65%, e.g., at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2, operably linked to one or more control sequences that direct the production of a variant under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants, such as a mannanase enzyme assay as described in Example 2. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant.

Methods or Uses

Methods for Improving the Nutritional Value of Animal Feed

The present invention further relates to a method for improving the nutritional value of an animal feed comprising plant based material, comprising adding to the feed a mannanase variant.

The term improving the nutritional value of an animal feed means improving the availability of nutrients in the feed. The nutritional values refers in particular to improving the solubilization and degradation of the arabinoxylan-containing fraction (e.g., such as hemicellulose) of the feed, thereby leading to increased release of nutrients from cells in the endosperm that have cell walls composed of highly recalcitrant hemicellulose. Consequently, an increased release of arabinoxylan oligomers indicates a disruption of the cell walls and as a result the nutritional value of the feed is improved resulting in increased growth rate and/or weight gain and/or feed conversion (i.e., the weight of ingested feed relative to weight gain). In addition the arabinoxylan oligomer release may result in improved utilization of these components per se either directly or by bacterial fermentation in the hind gut thereby resulting in a production of short chain fatty acids that may be readily absorbed in the hind and utilised in the energy metabolism.

Compositions of the Invention

The present invention also relates to compositions comprising a polypeptide variant of the present invention. Accordingly, the present invention relates to compositions comprising variant comprising a modification at one position corresponding to a position selected from the positions 1, 2, 3, 4, 5, 6, 8, 9, 10, 11, 13, 14, 15, 16, 17, 18, 19, 21, 23, 30, 32, 33, 34, 35, 37, 38, 39, 41, 44, 45, 47, 57, 59, 60, 62, 63, 65, 66, 67, 68, 70, 71, 74, 77, 78, 79, 80, 81, 82, 83, 93, 95, 96, 97, 98, 100, 104, 107, 108, 110, 111, 114, 115, 116, 118, 119, 131, 132, 133, 135, 136, 139, 142, 143, 146, 147, 150, 152, 154, 164, 167, 169, 172, 173, 174, 175, 176, 177, 180, 181, 183, 184, 185, 196, 199, 200, 201, 202, 203, 205, 206, 210, 212, 213, 214, 215, 226, 228, 229, 230, 234, 235, 241, 242, 243, 244, 245, 250, 254, 257, 258, 259, 260, 261, 262, 266, 267, 268, 270, 271, 272, 273, 276, 279, 280, 283, 285, 286, 288, 289, 290, 292, 293, 294, 295, and 296, of the polypeptide of SEQ ID NO: 2, wherein each modification is independently a substitution or a deletion, wherein said variant has at least 65%, e.g., at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2. Preferably, the compositions are enriched in such a variant. The term "enriched" means that the mannanase activity of the composition has been increased, e.g., with an enrichment factor of 1.1.

The composition may comprise a polypeptide variant as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, e.g., *Aspergillus aculeatus, Aspergillus awamori, Aspergillus foetidus, Aspergillus fumigatus, Aspergillus japonicus, Aspergillus nidulans, Aspergillus niger,* or *Aspergillus oryzae; Fusarium*, e.g., *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium suiphureum, Fusarium toruloseum, Fusarium trichothecioides,* or *Fusarium venenatum; Humicola*, e.g., *Humicola insolens* or *Humicola lanuginosa*; or *Trichoderma*, e.g., *Trichoderma harzianum, Trichoderma koningii, Trichoderma longibrachiatum, Trichoderma reesei,* or *Trichoderma viride.*

The compositions may be prepared in accordance with methods known in the art and may be in the form of a liquid or a dry composition. For instance, the composition may be in the form of a granulate or a microgranulate. The polypeptide variant may be stabilized in accordance with methods known in the art.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries. Thus, the present invention also relates to a detergent additive comprising a variant of the invention, optionally in the form of a non-dusting granulate, stabilized liquid, or protected enzyme. Accordingly, the present invention relates to a detergent additive comprising polypeptide having mannanase activity and which exhibits an improved wash performance and optionally an improved stability compared to the parent polypeptide, said variant comprises at least one modification in the amino acid motif QSRX1X2X3NR, wherein X1 is Q, K, or R, X2 is L or F, and X3 is A, N, or Q (SEQ ID NO: 2), corresponding to amino acid positions 169 to 176 of SEQ ID NO: 1, and has at least 75% sequence identity to said parent polypeptide, optionally, wherein the detergent additive is in the form of a non-dusting granulate, stabilized liquid, or protected enzyme.

In one aspect, the present invention relates to detergent compositions comprising a polypeptide variant of the present invention in combination with one or more additional cleaning composition components. Accordingly, the present invention relates to a detergent composition comprising variant comprising a modification at one position corresponding to a position selected from the positions 1, 2, 3, 4, 5, 6, 8, 9, 10, 11, 13, 14, 15, 16, 17, 18, 19, 21, 23, 30, 32, 33, 34, 35, 37, 38, 39, 41, 44, 45, 47, 57, 59, 60, 62, 63, 65, 66, 67, 68, 70, 71, 74, 77, 78, 79, 80, 81, 82, 83, 93, 95, 96, 97, 98, 100, 104, 107, 108, 110, 111, 114, 115, 116, 118, 119, 131, 132, 133, 135, 136, 139, 142, 143, 146, 147, 150, 152, 154, 164, 167, 169, 172, 173, 174, 175, 176, 177, 180, 181, 183, 184, 185, 196, 199, 200, 201, 202, 203, 205, 206, 210, 212, 213, 214, 215, 226, 228, 229, 230, 234, 235, 241, 242, 243, 244, 245, 250, 254, 257, 258, 259, 260, 261, 262, 266, 267, 268, 270, 271, 272, 273, 276, 279, 280, 283, 285, 286, 288, 289, 290, 292, 293, 294, 295, and 296, of the polypeptide of SEQ ID NO: 2, wherein each modification is independently a substitution or a deletion, wherein said variant has at least 65%, e.g., at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2, in combination with one or more additional cleaning composition component.

The choice of additional components is within the skill of the artisan and includes conventional ingredients, including the exemplary non-limiting components set forth below.

The choice of components may include, for textile care, such as laundry, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Accordingly, the present invention also relates to a composition which is a cleaning composition.

A composition according to the present invention may further comprise a detergent component, such as a surfactant, a bleach, a dispersant polymer such as a sulfonated polymer, a complexing agent, a bleach catalyst such as a manganese bleach catalyst, a crystal growth inhibitor, and/or fabric hueing agents.

In one embodiment, the composition is a phosphate free composition.

The detergent composition of the invention may for example be directed to an ADW (Automatic Dish Wash) composition comprising an enzyme of the present invention in combination with one or more additional ADW composition components. The choice of additional components is within the skill of the artisan and includes conventional ingredients, including the exemplary non-limiting components set forth below. Accordingly, in one aspect, the invention relates to a manual or automatic dishwashing detergent composition comprising a variant of the invention, and optionally a surfactant.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. Accordingly, in one aspect, the present invention relates to a manual or automatic laundry detergent composition comprising a variant according to the invention.

In a specific aspect, the invention provides a detergent concentrate/additive comprising the polypeptide of the invention. The detergent additive, as well as the detergent composition, may comprise one or more other enzymes such as an amylase, protease, a lipase, a peroxidase, another amylolytic enzyme, e.g., alpha-amylase, glucoamylase, maltogenic amylase, CGTase and/or a cellulase, another mannanase, pectinase, pectin lyase, cutinase, and/or laccase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like pro-teases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274. Preferred commercially available protease enzymes include ALCALASE®, SAVINASE® (SEQ ID NO: 3), PRIMASE®, DURALASE®, ESPERASE®, and KANNASE® (from Novozymes A/S), MAXATASE®, MAXACAL, MAXAPEM®, PROPERASE®, PURAFECT®, PURAFECT OXP®, FN2®, FN3®, FN4® (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al. (1993), *Biochemica et Biophysica Acta*, 1131:253-360), *B. stearothermophilus* (JP 64/744992) or *B. pumilus* (WO 91/16422). Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™ and LIPOLASE ULTRA™ (Novozymes A/S).

Amylases: Suitable amylases (alpha and/or beta) include those of bacterial or fungal origin. Chemically modified or protein engineered mutants are included. Amylases include, for example, alpha-amylases obtained from *Bacillus*, e.g., a special strain of *B. licheniformis*, described in more detail in GB 1,296,839. Examples of useful alpha-amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially available alpha-amylases are DURAMYL™, LIQUEZYME™, TERMAMYL™, NATALASE™, FUNGAMYL™ and BAN™ (Novozymes A/S), Preferenz S100, Preferenz S110, Preferenz S1000 (SEQ ID NO: 11), Excellenz S110, Excellenz S1000, Excellenz S2000, RAPIDASE™ and PURASTAR™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259. Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include CELLUZYME®, and CAREZYME® (Novozymes A/S), CLAZINASE®, and PURADAX HA® (Genencor International Inc.), and KAC-500(B)® (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include GUARDZYME® (Novozymes A/S).

Lechinases/Beta-glucanases: Suitable Lechinases include those of bacterial or fungal origin. They may be chemically modified or protein engineered. Examples of useful beta-glucanases include those described in WO 2015/144824 (Novozymes A/S) and WO 99/06516 (Henkel KGAA).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238 216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually comprise from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually comprise from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid mono-ethanolamide, polyhydroxy alkyl fatty acid amide, or N-acyl N-alkyl derivatives of glucosamine ("glucamides").

The detergent may comprise 0-65% of a detergent builder or complexing agent such as MGDA, GLDA, zeolite, diphosphate, triphosphate, phosphonate, carbonate, citrate, nitrilotriacetic acid, ethylenediaminetetraacetic acid, diethylenetri-aminepen-taacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinyl-pyrrolidone), poly (ethylene glycol), poly(vinyl alcohol), poly (vinylpyridine-N-oxide), poly(vinylimidazole), polycarboxylates such as sulfonated polymers, polyacrylates, maleic/acrylic acid copolymers and lauryl methacrylate/acrylic acid co-polymers.

The detergent may contain a bleaching system, which may comprise a $H_2O_2$ source such as perborate or percarbonate which may be combined with a peracid-forming bleach activator such as bleach catalysts, e.g. Mn-based or Co-based, tetraacetylethylenediamine or nonanoyloxybenzenesul-fonate. Alternatively, the bleaching system may comprise peroxyacids of, e.g., the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil re-deposition agents, dyes, bactericides, optical brighteners, hydrotropes, tarnish inhibitors, or perfumes.

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent composition may comprise about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry/ADW/hard surface cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent may comprise 0-30% by weight, such as about 1% to about 20%, of a bleaching system. Any bleaching system known in the art for use in laundry/ADW/hard surface cleaning detergents may be utilized. Suitable bleaching system components include bleaching catalysts, photobleaches, bleach activators, sources of hydrogen peroxide such as sodium percarbonate, sodium perborates and hydrogen peroxide-urea (1:1), preformed peracids and mixtures thereof. Suitable preformed peracids include, but are not limited to, peroxycarboxylic acids and salts, diperoxydicarboxylic acids, perimidic acids and salts, peroxymonosulfuric acids and salts, for example, Oxone®, and mixtures thereof.

Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable examples are tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that it is environmentally friendly Furthermore acetyl triethyl citrate and triacetin have good hydrolytical stability in the product upon storage and are efficient bleach activators. Finally ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

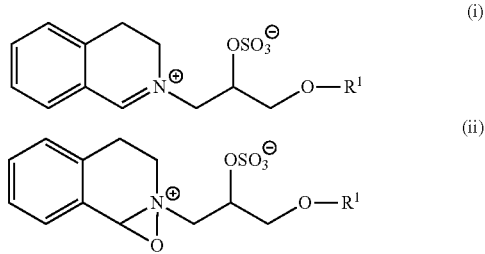

(iii) and mixtures thereof;
wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Preferably the bleach component comprises a source of peracid in addition to bleach catalyst, particularly organic bleach catalyst. The source of peracid may be selected from (a) preformed peracid; (b) percarbonate, perborate or persulfate salt (hydrogen peroxide source) preferably in combination with a bleach activator; and (c) perhydrolase enzyme and an ester for forming peracid in situ in the presence of water in a textile or hard surface treatment step.

The detergent may comprise 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

The detergent compositions of the present invention may also comprise fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

It is at present contemplated that in the detergent compositions any enzyme, in particular the alpha amylase polypeptides of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The alpha amylase polypeptides of the invention may additionally be incorporated in the detergent formulations disclosed in WO 2006/002643, which is hereby incorporated as reference.

Uses

The present invention is also directed to methods for using a polypeptide variant of the invention. The use may be in detergents, in particular laundry detergent compositions and dishwashing detergent compositions. Accordingly, the present invention relates to use of a variant comprising a modification at one position corresponding to a position selected from the positions 1, 2, 3, 4, 5, 6, 8, 9, 10, 11, 13, 14, 15, 16, 17, 18, 19, 21, 23, 30, 32, 33, 34, 35, 37, 38, 39, 41, 44, 45, 47, 57, 59, 60, 62, 63, 65, 66, 67, 68, 70, 71, 74, 77, 78, 79, 80, 81, 82, 83, 93, 95, 96, 97, 98, 100, 104, 107, 108, 110, 111, 114, 115, 116, 118, 119, 131, 132, 133, 135, 136, 139, 142, 143, 146, 147, 150, 152, 154, 164, 167, 169, 172, 173, 174, 175, 176, 177, 180, 181, 183, 184, 185, 196, 199, 200, 201, 202, 203, 205, 206, 210, 212, 213, 214, 215, 226, 228, 229, 230, 234, 235, 241, 242, 243, 244, 245, 250, 254, 257, 258, 259, 260, 261, 262, 266, 267, 268, 270, 271, 272, 273, 276, 279, 280, 283, 285, 286, 288, 289, 290, 292, 293, 294, 295, and 296, of the polypeptide of SEQ ID NO: 2, wherein each modification is independently a substitution or a deletion, wherein said variant has at least 65%, e.g., at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2.

Thus, the invention provides the use of a polypeptide variant of a parent polypeptide or composition of the invention, in a domestic or industrial cleaning process. In particular, the invention relates to use of a polypeptide variant according to the invention in laundry, dishwash; such as automatic or manual dishwash, hard surface cleaning, industrial and institutional cleaning, textile desizing, starch modification, starch liquefaction, saccharification, feed, baking, or brewing.

In one embodiment, the use is cleaning of fabric, for example laundry.

In another embodiment, the use is cleaning of ceramic, plastic or glass material, for example dishwashing.

Accordingly, the polypeptide variants of the invention are applicable as a component in washing, dishwashing, and hard surface cleaning detergent compositions (in either a domestic or industrial setting).

The Invention Defined in the Following Paragraphs

Paragraph 1: An isolated mannanase variant, or recombinant polypeptide or an active fragment thereof, wherein comprising a modification at one or more positions corresponding to a position selected from the positions 8, 9, 11, 13, 18, 21, 34, 37, 45, 47, 65, 100, 101, 104, 107, 108, 110, 114, 115, 116, 132, 133, 142, 147, 152, 154, 164, 169, 173, 174, 176, 177, 180, 183, 185, 196, 199, 201, 202, 205, 206, 210, 215, 226, 229, 231, 239, 243, 245, 257, 260, 267, 270, 275, 278, 282, 283, 284, 288, 292, 293, and 295 of the polypeptide of SEQ ID NO: 2, wherein each modification is independently a substitution, insertion, or deletion, wherein said variant has at least 59%, e.g. at least 60%, e.g. at least 65%, e.g., at least 70%, at least 75%, at least 80%, at least 85%, at least 90%, at least 95%, at least 96%, at least 97%, at least 98%, or at least 99%, but less than 100% sequence identity to the polypeptide of SEQ ID NO: 1, the polypeptide of SEQ ID NO: 2, or the polypeptide of SEQ ID NO:3; and wherein said variant, polypeptide or fragment has mannanase activity.

Paragraph 2: The variant, polypeptide, or fragment thereof according to paragraph 1, wherein said alteration is a substitution, wherein said substitution of the naturally-occurring amino acid residue at the one or more positions is a substitution with a different amino acid residue wherein said substitution produces a mannanase variant having a Half-life Improvement Factor (HIF) of ≥1.0 for a measure of stability.

Paragraph 3: The variant, polypeptide, or fragment thereof of paragraph 1, wherein said alteration is an insertion, wherein said insertion of the naturally-occurring amino acid residue at the one position produces a mannanase variant having a HIF of ≥1.0 for a measure of stability.

Paragraph 4: The variant, polypeptide, or fragment thereof of paragraph 1, wherein said alteration is a deletion, wherein said deletion of the naturally-occurring amino acid residue at the one position produces a mannanase variant having a HIF of ≥1.0 for a measure of stability.

Paragraph 5: The variant, polypeptide, or fragment thereof according to any one of the preceding paragraphs, wherein said variant, polypeptide, or fragment thereof has an improved detergent stability, improved protease stability and/or improved thermostability.

Paragraph 6: The variant, polypeptide, or fragment thereof according to any one of the preceding paragraphs, wherein said variant, polypeptide, or fragment thereof comprises a substitution or deletion at one position corresponding to positions 8, 9, 11, 13, 18, 21, 34, 37, 45, 47, 65, 100, 101, 104, 107, 108, 110, 114, 115, 116, 132, 133, 142, 147, 152, 154, 164, 169, 173, 174, 176, 177, 180, 183, 185, 196, 199, 201, 202, 205, 206, 210, 215, 226, 229, 231, 239, 243, 245, 257, 260, 267, 270, 275, 278, 282, 283, 284, 288, 292, 293, and 295 of the polypeptide of SEQ ID NO: 2, and wherein said substitution or deletion of the naturally-occurring amino acid residue at the one or more positions produces a mannanase variant having a HIF≥1.0 for a measure of stability at pH 8.0.

Paragraph 7: The variant, polypeptide, or fragment according to any one of the preceding paragraphs, wherein the different amino acid residue is selected from the group consisting of A, C, D, E, F, G, H, I, K, L, M, N, P, Q, R, S, T, V, W, and Y, with the proviso that the different amino acid residue is different from the naturally-occurring amino acid residue.

Paragraph 8: The variant, polypeptide, or fragment thereof according to any one of paragraphs 1, 2, 5 to 7, wherein said variant, polypeptide, or fragment thereof comprises one or more of the following substitutions versus the polypeptide of SEQ ID NO: 1 or the polypeptide of SEQ ID NO: 2: S8A, S8D, S8E, S8I, S8K, S8L, S8M, S8R, S8T, G9L, G9Q, G9R, G9S, G9V, G9W, G9Y, K11A, K11M, K11Q, K11R, K11S, K11V, Y13F, Y13I, Y13M, K18A, K18F, K18L, K18Q, K18R, K18S, V21I, V21M, N34C, N34E, N37C, N37D, N37H, N37Y, N37G, N37Q, K45A, K45C, K45D, K45E, K45G, K45H, K45M, K45N, K45Q, K45R, K45S, K45T, G47A, G47D, G47L, G47Q, G47R, G47S, D65P, D100G, D100K, D100L, A101C, A101E, A101L, A101N, A101M, A101Q, N104I, N104L, N104T, N104V, N104Y, N104C, N104M, N104Q, N104W, I107C, I107V, S108A, S108D, S108E, S108F, S108G, S108V, S108W, S108Y, K110A, K110G, K110H, K110N, K110Q, K110C, K110L, K110M, K110S, K110T, I114A, I114C, I114F, I114G, I114H, I114L, I114M, I114N, I114Q, I114R, I114T, I114V, I114W, I114Y, G115C, G115D, G115F, G115H, G115M, G115R, G115W, K116L, K116M, K116V, W132O, W132E, W132M, W132Q, W132Y, N133A, N133C, N133D, N133F, N133G, N133K, N133L, N133M, N133R, N133S, N133T, N133W, K142F, K142L, K142C, K142E, K142I, K142M, K142Q, K142R, K142V, K142W, K142Y, K147H, K147I, K147S, G152C, G152E, G152M, G152N, G152Q, G152R, G152S, K154A, K154D, K154E, K154F, K154G, K154H, K154L, K154M, K154T, K154W, W164D, W164F, W164M, W164Q, W164S, W164Y, Q169A, Q169M, D1730, D173E, Y174F, Q176A, Q1760, Q176E, Q176G, Q176H, Q176K, Q176L, Q176M, Q176R, Q176P, S177A, S177C, S177D, S177E, S177H, S177I, S177L, S177Q, S177R, S177T, S177V, A180E, A180Q, S183A, S183D, S183E, S183G, S183I, S183P, S183R, S183V, S183W, K185G, K185S, K185T, K185V, K185W, K185Y, Y196I, Y196V, K199A, A201E, A202C, A202K, A202M, A202P, A202R, A202W, K205A, K205C, K205D, K205L, K205N, K205S, A206L, A206M, A206F, A206T, N210A, N210G, N210S, G215M, Y226C, Y226G, Y226K, Y226N, Y226Q, Y226R, Y226S, Y226T, Y226W, N229C, D231P, D231T, R239F, R239Y, E243F, E243M, E243W, G245A, G245C, G245E, G245K, G245M, G245N, G245Q, G245R, S257A, S257C, S257D, S257E, S257G, S257H, S257K, S257P, S257V, L260C, L260F, L260K, L260M, L260Q, L260Y, L260T, T267D, T267E, N270A, N270C, N270D, S275A, S275D, S275E, S275K, S275P, S275Q, S275T, S275V, N278C, N278D, N278E, N278H, N278W, N282C, N282F, N282Y, D283G, D283S, D283W, T284E, T284I, K288A, K288R, Q292E, Q292I, Q292M, Q292R, Q292V, K293I, K293L, K293P, K293R, and G295S.

Paragraph 9: The variant, polypeptide, or fragment thereof according to any one of the preceding paragraphs, wherein the parent polypeptide has at least 59%, e.g. at least 60%, e.g., at least 62%, at least 63%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 1, the polypeptide of SEQ ID NO: 2, the polypeptide of SEQ ID NO: 3, or the polypeptide of SEQ ID NO: 4.

Paragraph 10: The variant, polypeptide, or fragment thereof according to paragraph 9, wherein said parent polypeptide is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to the polypeptide coding sequence of SEQ ID NO: 1.

Paragraph 11: The variant, polypeptide, or fragment thereof according to paragraph 9, wherein said parent polypeptide is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to the polypeptide coding sequence of SEQ ID NO: 2.

Paragraph 12: The variant, polypeptide, or fragment thereof according to paragraph 9, wherein said parent polypeptide is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to the polypeptide coding sequence of SEQ ID NO: 3.

Paragraph 13: The variant, polypeptide, or fragment thereof according to paragraph 9, wherein said parent polypeptide is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to the polypeptide coding sequence of SEQ ID NO: 4.

Paragraph 14: The variant, polypeptide, or fragment thereof according to any one of paragraphs 9 or 10, wherein said parent polypeptide comprises or consists of the polypeptide of SEQ ID NO: 1.

Paragraph 15: The variant, polypeptide, or fragment thereof according to any one of paragraphs 9 to 10, wherein said parent polypeptide is a fragment of the polypeptide of SEQ ID NO: 1, wherein said fragment has mannanase activity.

Paragraph 16: The variant, polypeptide, or fragment thereof according to any one of the preceding paragraphs, which has at least 60%, e.g., at least 65%, at least 70%, at least 75%, at least 80%, at least 85%, at least 90%, at least 95% identity, at least 96%, at least 97%, at least 98%, or at least 99%, but less than 100%, sequence identity to the amino acid sequence of the parent polypeptide.

Paragraph 17: The variant, polypeptide, or fragment thereof according to any one of the preceding paragraphs, wherein said variant, polypeptide, or fragment thereof consists of 250 to 300, e.g., 260 to 300, 270 to 300, 285 to 300 amino acids.

Paragraph 18: The variant, polypeptide, or fragment thereof according to any one of the preceding paragraphs, which has an improved property relative to the parent polypeptide, wherein said improved property is selected from the group consisting of catalytic efficiency, catalytic rate, chemical stability, oxidation stability, in-detergent stability, pH activity, pH stability, specific activity, stability under storage conditions, substrate binding, substrate cleavage, substrate specificity, substrate stability, surface properties, thermal activity, and thermostability.

Paragraph 19: The variant, polypeptide, or fragment thereof according to any one of the preceding paragraphs, wherein said mannanase activity is in the presence of a protease and/or a detergent component and/or detergent composition.

Paragraph 20: The variant, polypeptide, or fragment thereof according to paragraph 19, wherein said mannanase activity is in the presence of a protease.

Paragraph 21: The variant, polypeptide, or fragment thereof according to paragraph 19, wherein said mannanase activity is in the presence of a detergent component, such as a surfactant, a chelator, and a bleach.

Paragraph 22: The variant, polypeptide, or fragment thereof according to paragraph 19, wherein said mannanase activity is in the presence of a detergent composition.

Paragraph 23: The variant, polypeptide, or fragment thereof according to paragraphs 19 or 20, wherein said protease is a protease having at least 60% sequence identity to the polypeptide of SEQ ID NO: 5.

Paragraph 24: A composition comprising a variant, polypeptide, or fragment thereof according to any one of the preceding paragraphs.

Paragraph 25: The composition according to paragraph 24, wherein said composition further comprises an additional enzyme, such as a protease.

Paragraph 26: The composition according to any one of paragraphs 24 or 25, wherein said composition is a cleaning composition.

Paragraph 27: The composition according to any one of paragraphs 24 to 26, wherein said composition further comprises a surfactant, a bleaching system, a chelating agents, stabilizing agents, hydrotopes, builders, co-builders, bleach activators, polymers and/or fabric-huing agents.

Paragraph 28: The composition according to any one of paragraphs 24 to 27, wherein said composition comprises a surfactant, wherein said surfactant is selected from the group consisting of anionic surfactants, cationic surfactants, nonionic surfactants, and amphoteric surfactants.

Paragraph 29: The composition according to any one of the paragraph 24 to 28, wherein said composition is a detergent composition, such as a liquid laundry detergent composition, a powder laundry detergent composition, a liquid dishwash detergent composition, or a powder dishwash detergent composition.

Paragraph 30: The composition according to paragraph 29, wherein said composition is a liquid or powder laundry detergent composition.

Paragraph 31: The composition according to paragraph 29, wherein said composition is a liquid or powder automatic dishwashing (ADW) detergent composition.

Paragraph 32: The composition according to paragraph 29, wherein said composition is a liquid manual dishwashing detergent composition.

Paragraph 33: Use of a composition according to any one of the paragraphs 24 to 32 in a domestic or industrial cleaning process.

Paragraph 34: The use according to paragraph 33 for cleaning of fabric, for example laundry.

Paragraph 35: The use according to paragraph 33 for hard surface cleaning, for example dishwashing.

Paragraph 36: The use according to paragraph 33 for automated dishwashing.

Paragraph 37: An isolated polynucleotide encoding the variant according to any one of paragraphs 1 to 23.

Paragraph 38: A nucleic acid construct comprising the polynucleotide according to paragraph 37.

Paragraph 39: An expression vector comprising the polynucleotide according to paragraph 37.

Paragraph 40: A host cell comprising the polynucleotide according to paragraph 37.

Paragraph 41: A method of producing a mannanase variant, comprising:
  a. cultivating the host cell according to paragraph 40 under conditions suitable for expression of said variant; and
  b. recovering said variant.

Paragraph 42: A method for obtaining a mannanase variant, polypeptide or fragment thereof, comprising introducing into a parent polypeptide a substitution or a deletion at one position corresponding to a position selected from the positions 8, 9, 11, 13, 18, 21, 34, 37, 45, 47, 65, 100, 101, 104, 107, 108, 110, 114, 115, 116, 132, 133, 142, 147, 152, 154, 164, 169, 173, 174, 176, 177, 180, 183, 185, 196, 199, 201, 202, 205, 206, 210, 215, 226, 229, 231, 239, 243, 245, 257, 260, 267, 270, 275, 278, 282, 283, 284, 288, 292, 293, and 295 of the polypeptide of SEQ ID NO: 1, SEQ ID NO: 2, SEQ ID NO: 3, or SEQ ID NO: 4, wherein said variant, polypeptide or fragment thereof has mannanase activity; and recovering said variant, polypeptide or fragment thereof.

Paragraph 43: A method of dishwashing in an automatic dishwashing machine using a composition according to any one of paragraphs 24 to 29 and 31, comprising the steps of adding said composition in a detergent composition compartment in said automatic dishwashing machine, and releasing said composition during a main-wash cycle.

Paragraph 44: A method of laundering in an automatic laundering machine using a composition according to any one of paragraphs 24 to 30, comprising the steps of adding said composition in a detergent composition compartment in said automatic laundering machine, and releasing said composition during a main wash cycle.

Paragraph 45 An animal feed additive comprising the mannanase variant according to any one of paragraphs 1 to 23, and one or more components selected from the group consisting of:
  a) one or more vitamins;
  b) one or more minerals;
  c) one or more microbes;
  d) one or more amino acids; and
  e) one or more enzymes.

Paragraph 46: An animal feed comprising the mannanase variant according to any one of paragraphs 1 to 23, or the animal additive according to paragraph 45 and plant based material.

Paragraph 47: A method of improving the nutritional value of an animal feed, comprising adding to the feed the mannanase variant according to any one of paragraphs 1 to 23.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

EXAMPLES

Example 1: Site-Saturation Library Generation

The gene of PspMan4 was cloned into the *Bacillus subtilis* expression cassette and transformed in *Bacillus subtilis* expression host. Site-saturation libraries were generated by Mega PCR approach in each mentioned position in the PspMan4 gene with NNS doping in the forward mutagenic primer.

Two PCR reactions were performed 1) generation of C-terminal fragment with the flanking C-terminal reverse primer and the forward mutagenic primer 2) generation of Mega PCR product using the C-terminal fragment as the reverse mega-primer and the flanking N-terminal forward primer to give the full-length cassette. The Mega PCR product was then transformed in to the *Bacillus* host, where site-specific homologous recombination in the *Bacillus* chromosome takes place.

After 18-20 hours of growth in LB agar media with appropriate antibiotic, the transformed colonies were picked and inoculated in to the aqueous growth media. After 3 days of growth, culture PCR was carried out by initial heat lysis of cells, followed by PCR. The PCR products were sequence confirmed and the unique substitutions given for screening assays. The polymerase used for the PCR reaction was Phusion DNA polymerase (ThermoScientific, Cat. No.: F530L).

Example 2: Detergent Stability in 50% Model A Detergent

The Site-saturation library generated variants were tested for detergent stability in 50% Model A detergent after incubation at 30° C. for 120 mins. A buffer solution was prepared: 1M MOPS, pH 8-Stock solution of 1M MOPS was prepared by adding 209.06 g of MOPS (Sigma, M1254) in 1 L of Milli-Q water and adjusting pH to 8 using 5M NaOH solution. The working stock of 100 mM MOPS was prepared by adding 100 ml of 1M MOPS and making up volume to 1 L using Milli-Q water. The stock solution of 1% Triton-X100 was made by adding 1 ml of Triton-X100 (Sigma T8787) 99 ml of Milli-Q water.

Enzyme Dilution Buffer (EDB)—100 mM MOPS, pH 8+0.01% Triton-X100

A substrate solution was prepared by adding 1 g of powdered Mannazyme tablet (Megazyme, T-MNZ-200T) in 100 ml of EDB and mixing the solution. Substrate plates were prepared in 96 Well Nunc plate, dispensing 180 μl of substrate solution while mixing.

Purified protein samples used for assay controls were as below in Table 1 and 2.

TABLE 1

Enzymes used as assay controls

| Mannanase polypeptide | Conc. (mg/ml) |
|---|---|
| Reference (SEQ ID NO: 2) | 0.93 |
| Benchmark (Mannaway) | 0.6 |

TABLE 2

Protease used in assays for determination of protease stability.

| | Stock Protease conc. (mg/ml) |
|---|---|
| Protease (SEQ ID NO: 5 with the following modifications: S9E + N42R + N74D + V199I + Q200L + Y203W + S253D + N255W + L256E | 52 |

Detergent:

Model A detergent (composition shown below in Table 3) was used for screening. The native pH of detergent was 8. Model A has 33.6 wt % of water content and 11.6 wt % of LAS (the commercial LAS has a purity of 97%, of which 12 wt % is added giving the final concentration of 11.6 wt % of the final composition). In Table 3 below is listed the detergent stock solutions to be prepared for required concentration during sample setup.

TABLE 3

Model A detergent composition

| Ingredient (abbreviation) | Explanation | wt % |
|---|---|---|
| LAS (purity of 97%) | (C10-C13)alkylbenzene-sulfonic acid | 12.00 |
| SLES | sodium lauryl ether sulfate | 17.63 |
| Soy soap | | 2.75 |
| Coco soap | | 2.75 |
| AEO | alcohol ethoxylate | 11.00 |
| NaOH | Sodium hydroxide | 1.75 |
| Ethanol | | 2.70 |
| Isopropanol | | 0.30 |
| MPG | monopropylene glycol | 6.00 |
| Glycerol | | 1.71 |
| TEA | triethanolamine | 3.33 |
| Sodium formate | | 1.00 |
| Sodium citrate | | 2.00 |
| DTMPA | diethylenetriaminepentakis(methylene)pentakis (phosphonic acid), heptasodium salt | 0.48 |
| PCA | polycarboxylic acid type polymer, sodium salt | 0.46 |
| Phenoxyethanol | | 0.50 |
| Ion exchanged water | | 33.64 |

TABLE 4

Detergent stock solutions

| Target Det. Conc. (%) | Stock det. conc. (%) |
|---|---|
| 50 | 56 |

A Model A detergent stock solution of 56 vol % was made using 100 mM MOPS pH 8.0 (as described above). 90 μl of Model A detergent stock solution was dispersed into the 96 Well plates (Nunc, 260836). 10 ul of enzyme or culture supernatant was added to the detergent plates and mixed at 1000 rpm for 15 mins in a Mixmate, Eppendorf 5353. Duplicate of plates was generated; one stored at 4° C. (Un-stress) and another stored at 30° C. (Stress). For stress setup, sample to Model A detergent ratio was maintained to 1:9 (measured as Vol %). The plates were incubated for 120 mins in a temperature controlled incubator (Scigenics Biotech (20° C.-45° C.)), followed by assaying for Mannanase activity.

Mannanase activity was measured by preparing a sample dilution: the samples were diluted 5× in EDB. 20 μl of diluted sample was added to 180 μl of substrate in a new 96 Well plate. The plate was mixed for 20 mins at 800 rpm at 25° C. followed by 10 mins settling. 50 μl of the supernatant from the mixture was transferred to a 384 well plate (Nunc, 262160) and absorbance was read at 590 nm in reader (Infinite M1000, Tecan).

TABLE 5

Variants tested and half-life improvement factors (HIF)

| Mutation | HIF | Mutation | HIF |
|---|---|---|---|
| S8A | 1.3 | K142L | 1.1 |
| S8D | 1.0 | K142Y | 1.3 |
| S8E | 1.0 | K147H | 1.0 |
| S8I | 1.1 | G152C | 1.2 |
| S8K | 1.2 | G152E | 1.4 |
| S8R | 1.0 | G152M | 1.1 |
| G9L | 1.2 | G152N | 1.6 |
| G9Q | 1.3 | G152Q | 1.3 |
| G9S | 1.4 | G152R | 1.2 |
| G9V | 1.5 | G152S | 1.2 |
| G9W | 1.2 | K154D | 1.0 |
| G9Y | 1.2 | K154E | 1.1 |
| K11A | 1.1 | W164M | 1.0 |
| K11M | 1.1 | Q169A | 1.1 |
| K11Q | 1.0 | D173C | 1.0 |
| K11R | 1.1 | Q176P | 1.0 |
| K11S | 1.0 | S177A | 1.0 |
| Y13F | 1.1 | S177H | 1.2 |
| Y13I | 1.1 | S177L | 1.1 |
| Y13M | 1.1 | S177T | 1.1 |
| K18A | 1.2 | S177V | 1.2 |
| K18F | 1.2 | S183E | 1.1 |
| K18L | 1.3 | S183G | 1.2 |
| K18S | 1.0 | S183I | 1.1 |
| N34C | 1.3 | S183R | 1.1 |
| N34E | 2.0 | S183V | 1.0 |
| N37H | 1.1 | S183W | 1.0 |
| N37Y | 1.1 | K199A | 1.0 |
| K45A | 1.6 | A201E | 1.5 |
| K45C | 1.5 | A202C | 1.3 |
| K45D | 1.6 | A202K | 1.1 |
| K45E | 1.6 | A202M | 1.5 |
| K45G | 1.3 | A202P | 1.4 |
| K45H | 1.0 | A202R | 1.5 |
| K45N | 1.5 | K205A | 1.0 |
| K45Q | 1.9 | K205C | 1.0 |
| K45R | 1.1 | K205D | 2.0 |
| K45S | 1.5 | K205N | 1.1 |
| K45T | 1.0 | K205S | 1.1 |

TABLE 5-continued

Variants tested and half-life improvement factors (HIF)

| Mutation | HIF | Mutation | HIF |
|---|---|---|---|
| G47A | 1.0 | A206T | 1.0 |
| G47D | 1.1 | N210A | 1.1 |
| G47L | 1.2 | Y226C | 1.3 |
| G47Q | 1.2 | Y226K | 1.0 |
| G47R | 1.2 | Y226N | 1.3 |
| G47S | 1.1 | N229C | 1.5 |
| D100L | 1.0 | D231P | 1.7 |
| A101M | 1.8 | R239F | 2.5 |
| A101Q | 1.2 | R239Y | 2.0 |
| N104C | 1.0 | E243W | 1.2 |
| N104M | 1.1 | G245C | 1.0 |
| N104Q | 1.2 | G245E | 1.4 |
| N104W | 1.0 | G245N | 1.2 |
| I107C | 1.0 | G245Q | 1.6 |
| I107V | 1.1 | G245R | 1.1 |
| S108A | 1.2 | S257C | 1.3 |
| S108D | 1.7 | S257D | 1.6 |
| S108Y | 1.4 | S257E | 2.1 |
| K110A | 1.1 | L260F | 1.1 |
| K110G | 1.0 | L260M | 1.1 |
| K110H | 1.1 | L260Y | 1.6 |
| K110N | 1.0 | N270A | 1.1 |
| K110Q | 1.0 | N270D | 1.8 |
| I114A | 1.2 | S275A | 1.3 |
| I114C | 1.2 | S275D | 1.9 |
| I114F | 1.1 | S275E | 2.0 |
| I114G | 1.1 | S275P | 1.3 |
| I114H | 1.3 | S275Q | 1.1 |
| I114L | 1.3 | S275T | 1.4 |
| I114M | 1.1 | S275V | 1.1 |
| I114N | 1.3 | N278C | 1.1 |
| I114Q | 1.2 | N278D | 1.3 |
| I114R | 1.2 | N278E | 1.4 |
| I114T | 1.2 | N278H | 1.1 |
| I114V | 1.3 | N282C | 1.5 |
| G115C | 1.2 | N282Y | 1.5 |
| G115F | 1.2 | D283S | 2.0 |
| G115H | 1.4 | K288A | 1.1 |
| G115M | 1.1 | K288R | 1.1 |
| G115R | 1.0 | Q292E | 1.3 |
| G115W | 1.1 | Q292I | 1.1 |
| K116L | 1.0 | Q292M | 1.1 |
| K116M | 1.1 | Q292V | 2.0 |
| K116V | 1.2 | K293A | 1.0 |
| N133A | 1.5 | K293C | 1.1 |
| N133C | 1.1 | K293H | 1.1 |
| N133D | 1.2 | K293I | 1.2 |
| N133G | 1.3 | K293L | 1.4 |
| N133K | 1.0 | K293P | 1.6 |
| N133S | 1.3 | K293R | 1.1 |
| K142F | 1.3 | G295S | 1.1 |

Example 3: Protease Stability at pH 8.0

The variants of the present invention were tested for protease stability at a pH of 8.0 following the set-up herein described.

A buffer solution was made by using 1M MOPS. A pH 8-Stock solution of 1M MOPS was prepared by adding 209.06 g of MOPS (Sigma, M1254) in 1 L of Milli-Q water and adjusting pH to 8 using 5M NaOH solution. A working stock solution of 100 mM MOPS was prepared by adding 100 ml of 1M MOPS and making up volume to 1 L using Milli-Q water. Another stock solution of 1% Triton-X100 was made by adding 1 ml of Triton-X100 (Sigma T8787) 99 ml of Milli-Q water.

An Enzyme Dilution Buffer (EDB) as described above was also made. EDB—100 mM MOPS, pH 8+0.01% Triton-X100.

Protein normalization Buffer—100 mM MOPS, pH 8

Substrate:

A substrate solution was prepared by adding 1 g of powdered Mannazyme tablet (Megazyme, T-MNZ-200T) in 100 ml of EDB and mixing the solution. Substrate plates were prepared in 96 Well Nunc plate, dispensing 180 µl of substrate solution while mixing.

Enzymes:

Purified protein samples used for assay controls were the variants of the present invention in a concentration of 0.93 mg/ml and a benchmark (commercially available from Novozymes A/S, Mannaway®) in a concentration of 0.6 mg/ml. The samples were incubated with a stock protease without any protease inhibitor in a concentration of 52 mg/ml. The protease used was a protease having SEQ ID NO: 5 and the modifications S9E+N42R+N74D+V199I+Q200L+Y203W+S253D+N255W+L256E.

Consumables:

96 Well plate (Nunc, 260836), 384 Well Plate (Nunc, 262160)

Sample Incubator:

Temperature controlled incubator, Scigenics Biotech (20° C.-45° C.)

Sample Setup:

For stress setup, sample to detergent (buffer) ratio was maintained to 1:9

| | |
|---|---|
| Buffer (Vol %) | 90 |
| Sample (Vol %) | 10 |

MOPS with Protease:

100 mM MOPS, pH 8 with concentration of 0.166 mg/ml was made using 52 mg/ml protease stock. Effective concentration of Protease in stress mix was 0.15 mg/ml.

Protocol:

90 µl of the protease buffer was dispensed into the 96 Well plates. The culture plates were centrifuged at 3000 rpm for 30 mins. Following 10 µl of culture supernatant were added to the 96 well plates and mixed at 800 rpm for 5 mins in a Mixmate. Two culture plates for each sample set were generated; one stored at 4° C. (Un-stress) and another stored at 37° C. (Stress). After 120 mins incubation, the plates were assayed for Mannanase activity. The samples were diluted 5× in EDB and 20 µl of diluted sample was added to 180 µl of substrate in a 96 Well plate. The 96 well plate was mixed for 20 mins at 800 rpm, 25° C. followed by 10 mins settling. 50 µl of supernatant from the mixture was transferred to 384 well plate and read at 590 nm in reader (Infinite M1000, Tecan).

TABLE 6

Tested variants and half-life improvement factors (HIF)

| Mutation | Position | % RA | IF | HIF |
|---|---|---|---|---|
| S8T | 8 | 34.85 | 1.0 | 1.0 |
| G9L | 9 | 38.20 | 1.2 | 1.2 |
| G9Q | 9 | 32.72 | 1.0 | 1.0 |
| G9R | 9 | 31.76 | 1.0 | 1.0 |
| G9V | 9 | 36.53 | 1.2 | 1.1 |
| K11V | 11 | 38.00 | 1.2 | 1.2 |
| Y13I | 13 | 36.98 | 1.2 | 1.2 |
| K18R | 18 | 33.80 | 1.1 | 1.1 |

TABLE 6-continued

Tested variants and half-life improvement factors (HIF)

| Mutation | Position | % RA | IF | HIF |
|---|---|---|---|---|
| K18S | 18 | 34.96 | 1.1 | 1.1 |
| V21I | 21 | 36.76 | 1.1 | 1.1 |
| V21M | 21 | 39.63 | 1.2 | 1.2 |
| N34E | 34 | 33.78 | 1.0 | 1.0 |
| N37G | 37 | 35.98 | 1.1 | 1.1 |
| N37Q | 37 | 40.40 | 1.2 | 1.2 |
| N37Y | 37 | 35.21 | 1.1 | 1.1 |
| K45R | 45 | 35.26 | 1.1 | 1.1 |
| G47Q | 47 | 39.38 | 1.2 | 1.2 |
| G47R | 47 | 53.40 | 1.6 | 1.7 |
| D65P | 65 | 40.83 | 1.3 | 1.3 |
| D100G | 100 | 34.86 | 1.2 | 1.2 |
| D100K | 100 | 32.39 | 1.1 | 1.1 |
| A101C | 101 | 34.09 | 1.1 | 1.1 |
| A101E | 101 | 41.52 | 1.4 | 1.4 |
| A101L | 101 | 35.27 | 1.2 | 1.2 |
| A101M | 101 | 42.00 | 1.4 | 1.4 |
| A101N | 101 | 30.43 | 1.0 | 1.0 |
| A101Q | 101 | 30.99 | 1.0 | 1.0 |
| N104I | 104 | 38.13 | 1.3 | 1.3 |
| N104L | 104 | 30.13 | 1.0 | 1.0 |
| N104T | 104 | 31.51 | 1.1 | 1.0 |
| N104V | 104 | 45.57 | 1.5 | 1.5 |
| N104Y | 104 | 31.40 | 1.1 | 1.0 |
| I107V | 107 | 33.49 | 1.1 | 1.1 |
| S108E | 108 | 54.24 | 1.8 | 2.0 |
| S108F | 108 | 33.61 | 1.1 | 1.1 |
| S108G | 108 | 30.75 | 1.0 | 1.0 |
| S108V | 108 | 42.69 | 1.4 | 1.4 |
| S108W | 108 | 36.34 | 1.2 | 1.2 |
| K110C | 110 | 31.77 | 1.1 | 1.1 |
| K110H | 110 | 39.62 | 1.3 | 1.3 |
| K110L | 110 | 36.04 | 1.2 | 1.2 |
| K110M | 110 | 30.47 | 1.0 | 1.0 |
| K110N | 110 | 30.46 | 1.0 | 1.0 |
| K110S | 110 | 38.53 | 1.3 | 1.3 |
| K110T | 110 | 38.90 | 1.3 | 1.3 |
| I114A | 114 | 45.38 | 1.3 | 1.4 |
| I114C | 114 | 37.10 | 1.1 | 1.1 |
| I114F | 114 | 37.84 | 1.1 | 1.1 |
| I114G | 114 | 46.45 | 1.4 | 1.4 |
| I114H | 114 | 36.20 | 1.1 | 1.1 |
| I114L | 114 | 37.06 | 1.1 | 1.1 |
| I114N | 114 | 35.23 | 1.0 | 1.0 |
| I114R | 114 | 40.78 | 1.2 | 1.2 |
| I114T | 114 | 39.91 | 1.2 | 1.2 |
| I114V | 114 | 37.59 | 1.1 | 1.1 |
| I114W | 114 | 36.30 | 1.1 | 1.1 |
| I114Y | 114 | 34.61 | 1.0 | 1.0 |
| G115C | 115 | 35.67 | 1.0 | 1.0 |
| G115D | 115 | 40.14 | 1.2 | 1.2 |
| G115M | 115 | 45.83 | 1.3 | 1.4 |
| G115W | 115 | 39.01 | 1.1 | 1.1 |
| K116L | 116 | 35.55 | 1.0 | 1.0 |
| K116M | 116 | 34.73 | 1.0 | 1.0 |
| K116V | 116 | 45.62 | 1.3 | 1.4 |
| W132Y | 132 | 30.75 | 1.0 | 1.0 |
| N133A | 133 | 52.55 | 1.7 | 1.8 |
| N133C | 133 | 47.56 | 1.6 | 1.6 |
| N133D | 133 | 51.46 | 1.7 | 1.8 |
| N133F | 133 | 40.93 | 1.3 | 1.3 |
| N133G | 133 | 42.21 | 1.4 | 1.4 |
| N133K | 133 | 37.63 | 1.2 | 1.2 |
| N133L | 133 | 34.88 | 1.1 | 1.1 |
| N133M | 133 | 40.30 | 1.3 | 1.3 |
| N133R | 133 | 42.42 | 1.4 | 1.4 |
| N133S | 133 | 40.20 | 1.3 | 1.3 |
| N133T | 133 | 35.68 | 1.2 | 1.1 |
| N133W | 133 | 39.69 | 1.3 | 1.3 |
| K142C | 142 | 41.99 | 1.4 | 1.4 |
| K142E | 142 | 43.58 | 1.4 | 1.4 |
| K142F | 142 | 36.43 | 1.2 | 1.2 |
| K142I | 142 | 33.02 | 1.1 | 1.1 |
| K142L | 142 | 34.30 | 1.1 | 1.1 |
| K142M | 142 | 32.85 | 1.1 | 1.1 |
| K142Q | 142 | 36.84 | 1.2 | 1.2 |
| K142R | 142 | 37.86 | 1.2 | 1.2 |
| K142V | 142 | 31.09 | 1.0 | 1.0 |
| K142W | 142 | 31.93 | 1.0 | 1.0 |
| K142Y | 142 | 52.82 | 1.7 | 1.9 |
| K147H | 147 | 38.20 | 1.3 | 1.2 |
| K147I | 147 | 32.85 | 1.1 | 1.1 |
| K147S | 147 | 35.56 | 1.2 | 1.1 |
| G152M | 152 | 31.10 | 1.0 | 1.0 |
| G152N | 152 | 49.52 | 1.6 | 1.7 |
| G152Q | 152 | 37.84 | 1.2 | 1.2 |
| K154A | 154 | 39.82 | 1.4 | 1.3 |
| K154D | 154 | 45.72 | 1.6 | 1.6 |
| K154E | 154 | 41.39 | 1.4 | 1.4 |
| K154F | 154 | 33.32 | 1.1 | 1.1 |
| K154G | 154 | 32.53 | 1.1 | 1.1 |
| K154H | 154 | 33.51 | 1.1 | 1.1 |
| K154L | 154 | 38.46 | 1.3 | 1.3 |
| K154M | 154 | 35.69 | 1.2 | 1.2 |
| K154T | 154 | 29.40 | 1.0 | 1.0 |
| K154W | 154 | 29.35 | 1.0 | 1.0 |
| W164D | 164 | 32.43 | 1.1 | 1.1 |
| W164F | 164 | 30.49 | 1.0 | 1.0 |
| W164M | 164 | 39.25 | 1.3 | 1.3 |
| Q169M | 169 | 30.46 | 1.0 | 1.0 |
| Y174F | 174 | 38.58 | 1.3 | 1.3 |
| Q176A | 176 | 41.73 | 1.4 | 1.4 |
| Q176C | 176 | 32.96 | 1.1 | 1.1 |
| Q176E | 176 | 32.67 | 1.1 | 1.1 |
| Q176G | 176 | 32.76 | 1.1 | 1.1 |
| Q176H | 176 | 36.07 | 1.2 | 1.2 |
| Q176K | 176 | 43.14 | 1.5 | 1.5 |
| Q176L | 176 | 37.91 | 1.3 | 1.3 |
| Q176M | 176 | 39.63 | 1.2 | 1.2 |
| Q176R | 176 | 32.50 | 1.0 | 1.0 |
| S177A | 177 | 34.96 | 1.1 | 1.1 |
| S177E | 177 | 34.34 | 1.1 | 1.1 |
| S177H | 177 | 35.42 | 1.1 | 1.1 |
| S177I | 177 | 32.58 | 1.0 | 1.0 |
| S177Q | 177 | 39.45 | 1.2 | 1.2 |
| S177R | 177 | 36.58 | 1.1 | 1.1 |
| A180E | 180 | 40.31 | 1.3 | 1.3 |
| A180Q | 180 | 35.00 | 1.1 | 1.1 |
| S183A | 183 | 35.81 | 1.1 | 1.1 |
| S183D | 183 | 34.15 | 1.1 | 1.1 |
| S183P | 183 | 35.34 | 1.1 | 1.1 |
| S183R | 183 | 47.13 | 1.5 | 1.5 |
| K185G | 185 | 40.92 | 1.3 | 1.3 |
| K185S | 185 | 44.49 | 1.4 | 1.4 |
| K185T | 185 | 44.59 | 1.4 | 1.4 |
| K185V | 185 | 35.96 | 1.1 | 1.1 |
| K185W | 185 | 34.02 | 1.1 | 1.1 |
| K185Y | 185 | 34.85 | 1.1 | 1.1 |
| A202W | 202 | 34.50 | 1.1 | 1.1 |
| K205D | 205 | 33.28 | 1.0 | 1.0 |
| K205N | 205 | 37.90 | 1.2 | 1.2 |
| A206L | 206 | 37.40 | 1.3 | 1.2 |
| A206M | 206 | 40.85 | 1.4 | 1.4 |
| A206F | 206 | 31.02 | 1.0 | 1.0 |
| N210G | 210 | 37.65 | 1.3 | 1.2 |
| N210S | 210 | 37.61 | 1.3 | 1.2 |
| G215M | 215 | 30.68 | 1.2 | 1.1 |
| Y226G | 226 | 39.55 | 1.5 | 1.4 |
| Y226W | 226 | 26.40 | 1.0 | 1.0 |
| R239F | 239 | 30.66 | 1.1 | 1.1 |
| R239Y | 239 | 35.62 | 1.3 | 1.2 |
| E243F | 243 | 30.53 | 1.1 | 1.1 |
| E243M | 243 | 38.92 | 1.4 | 1.3 |
| E243W | 243 | 55.60 | 2.2 | 2.4 |
| G245A | 245 | 29.88 | 1.2 | 1.2 |
| G245E | 245 | 34.39 | 1.4 | 1.3 |
| G245K | 245 | 31.88 | 1.3 | 1.3 |
| G245M | 245 | 30.83 | 1.2 | 1.2 |
| G245N | 245 | 27.47 | 1.1 | 1.1 |
| G245Q | 245 | 38.14 | 1.5 | 1.4 |
| G245R | 245 | 36.94 | 1.5 | 1.4 |
| S257C | 257 | 29.94 | 1.2 | 1.2 |

TABLE 6-continued

Tested variants and half-life improvement factors (HIF)

| Mutation | Position | % RA | IF | HIF |
|---|---|---|---|---|
| S257D | 257 | 40.93 | 1.6 | 1.6 |
| S257E | 257 | 57.24 | 2.3 | 2.5 |
| S257P | 257 | 67.11 | 2.8 | 3.5 |
| L260C | 260 | 24.90 | 1.0 | 1.0 |
| L260F | 260 | 26.72 | 1.1 | 1.1 |
| L260K | 260 | 44.32 | 1.8 | 1.7 |
| L260M | 260 | 31.11 | 1.3 | 1.2 |
| L260Q | 260 | 25.83 | 1.1 | 1.0 |
| L260Y | 260 | 27.29 | 1.1 | 1.1 |
| N270D | 270 | 40.53 | 1.7 | 1.6 |
| S275A | 275 | 40.30 | 1.2 | 1.2 |
| S275D | 275 | 46.35 | 1.4 | 1.5 |
| S275E | 275 | 64.54 | 2.0 | 2.6 |
| S275K | 275 | 33.35 | 1.0 | 1.0 |
| S275P | 275 | 62.03 | 1.9 | 2.4 |
| S275Q | 275 | 53.36 | 1.6 | 1.8 |
| N278E | 278 | 47.37 | 1.5 | 1.5 |
| N282F | 282 | 44.78 | 1.4 | 1.4 |
| N282Y | 282 | 57.63 | 1.8 | 2.0 |
| D283S | 283 | 31.33 | 1.2 | 1.2 |
| D283W | 283 | 48.78 | 1.9 | 1.9 |
| Q292I | 292 | 26.29 | 1.0 | 1.0 |
| Q292M | 292 | 27.65 | 1.1 | 1.1 |
| Q292R | 292 | 31.38 | 1.2 | 1.2 |
| Q292V | 292 | 26.74 | 1.1 | 1.0 |
| K293I | 293 | 31.64 | 1.1 | 1.1 |
| K293L | 293 | 38.54 | 1.3 | 1.3 |
| K293P | 293 | 32.27 | 1.1 | 1.1 |
| K293R | 293 | 31.06 | 1.0 | 1.0 |

Example 4: Thermostability, pH 8.0

The variants of the present invention were tested for thermostability at a pH of 8.0. following a set-up as described herein.

1M MOPS, pH 8-Stock solution of 1M MOPS was prepared by adding 209.06 g of MOPS (Sigma, M1254) in 1 L of Milli-Q water and adjusting pH to 8 using 5M NaOH solution. A working stock of 100 mM MOPS was prepared by adding 100 ml of 1M MOPS and making up volume to 1 L using Milli-Q water. A stock solution of 1% Triton-X100 was made by adding 1 ml of Triton-X100 (Sigma T8787) 99 ml of Milli-Q water.
An Enzyme Dilution Buffer (EDB) as described above was also made. EDB—100 mM MOPS, pH 8+0.01% Triton-X100.
Substrate:
Substrate solution was prepared by adding 1 g of powdered Mannazyme tablet (Megazyme, T-MNZ-200T) in 100 ml of EDB and mixing the solution. Substrate plates were prepared in 96 Well Nunc plate, dispensing 180 μl of substrate solution while mixing.
Enzymes:
Purified protein samples used for assay controls were the variants of the present invention in a concentration of 0.93 mg/ml and a benchmark (commercially available from Novozymes A/S, Mannaway®) in a concentration of 0.6 mg/ml.
Consumables:
96 Well plate (Nunc, 260836), 384 Well Plate (Nunc, 262160)
Sample Incubator:
Thermal cycler (T-Robot, Biometra)
Sample Setup:
For stress setup, sample to detergent (buffer) ratio was maintained to 1:9

| Buffer (Vol %) | 90 |
|---|---|
| Sample (Vol %) | 10 |

Protocol:
90 μl of 100 mM MOPS, pH8 was dispensed into 96 Well PCR plates. Culture plates were centrifuged at 3000 rpm for 30 mins. 10 μl of culture supernatant was added to detergent plates and mix by aspiration in Tecan. Two of these culture plates were generated; one stored at 4° C. (Un-stress) and another stored at 53° C. (Stress). After 40 mins incubation, the plates were assayed for Mannanase activity as described above. The samples were diluted 5× in EDB and 20 μl of diluted sample was added to 180 ul of substrate in a 96 Well plate. The plate was mixed for 20 mins at 800 rpm, 25° C. followed by 10 mins settling. 50 μl of supernatant from the mixture was transferred to 384 well plate and read at 590 nm in reader (Infinite M1000, Tecan).

TABLE 7

Tested variants and half-life improvement factors (HIF)

| Mutation | Position | % RA | IF | HIF |
|---|---|---|---|---|
| S8E | 8 | 40.60 | 1.4 | 1.4 |
| S8L | 8 | 28.73 | 1.0 | 1.0 |
| S8M | 8 | 29.10 | 1.0 | 1.0 |
| K11M | 11 | 36.07 | 1.2 | 1.2 |
| K11Q | 11 | 35.85 | 1.2 | 1.1 |
| K11V | 11 | 52.55 | 1.7 | 1.8 |
| Y13M | 13 | 32.32 | 1.0 | 1.0 |
| K18Q | 18 | 34.77 | 1.1 | 1.1 |
| V21I | 21 | 47.46 | 1.7 | 1.7 |
| N34E | 34 | 63.31 | 2.3 | 2.8 |
| N37C | 37 | 54.07 | 2.0 | 2.1 |
| N37D | 37 | 53.80 | 1.9 | 2.1 |
| N37G | 37 | 32.73 | 1.2 | 1.2 |
| N37H | 37 | 41.62 | 1.5 | 1.5 |
| N37Q | 37 | 54.27 | 2.0 | 2.1 |
| N37Y | 37 | 31.81 | 1.2 | 1.1 |
| K45A | 45 | 50.16 | 1.9 | 1.9 |
| K45D | 45 | 28.19 | 1.0 | 1.0 |
| K45E | 45 | 49.94 | 1.8 | 1.9 |
| K45G | 45 | 40.81 | 1.5 | 1.5 |
| K45M | 45 | 34.40 | 1.3 | 1.2 |
| K45N | 45 | 43.05 | 1.6 | 1.6 |
| K45Q | 45 | 62.51 | 2.3 | 2.8 |
| K45R | 45 | 42.48 | 1.6 | 1.5 |
| K45S | 45 | 27.67 | 1.0 | 1.0 |
| A101C | 101 | 39.61 | 1.2 | 1.2 |
| A101E | 101 | 68.53 | 2.1 | 3.0 |
| A101L | 101 | 38.25 | 1.2 | 1.2 |
| A101M | 101 | 51.22 | 1.6 | 1.7 |
| A101Q | 101 | 37.67 | 1.2 | 1.2 |
| S108D | 108 | 62.31 | 1.9 | 2.4 |
| S108E | 108 | 78.64 | 2.4 | 4.7 |
| K116M | 116 | 54.68 | 1.7 | 1.9 |
| W132C | 132 | 34.67 | 1.1 | 1.1 |
| W132E | 132 | 43.01 | 1.3 | 1.3 |
| W132M | 132 | 33.33 | 1.0 | 1.0 |
| W132Q | 132 | 77.68 | 2.4 | 4.5 |
| W132Y | 132 | 42.07 | 1.3 | 1.3 |
| N133A | 133 | 37.33 | 1.1 | 1.1 |
| N133C | 133 | 56.94 | 1.7 | 2.0 |
| N133D | 133 | 72.79 | 2.2 | 3.5 |
| N133S | 133 | 38.23 | 1.2 | 1.2 |
| K142I | 142 | 45.27 | 1.4 | 1.4 |
| K142Q | 142 | 36.14 | 1.1 | 1.1 |
| K142R | 142 | 46.69 | 1.4 | 1.5 |
| K154M | 154 | 52.37 | 2.0 | 2.1 |
| W164A | 164 | 36.08 | 1.4 | 1.3 |
| W164F | 164 | 45.90 | 1.7 | 1.8 |
| W164M | 164 | 42.38 | 1.6 | 1.5 |
| W164Q | 164 | 41.84 | 1.6 | 1.5 |
| W164S | 164 | 48.14 | 1.8 | 1.8 |
| W164Y | 164 | 54.08 | 2.0 | 2.2 |

TABLE 7-continued

Tested variants and half-life improvement factors (HIF)

| Mutation | Position | % RA | IF | HIF |
|---|---|---|---|---|
| D173E | 173 | 36.98 | 1.4 | 1.3 |
| Q176A | 176 | 30.08 | 1.1 | 1.1 |
| Q176E | 176 | 49.86 | 1.9 | 1.9 |
| S177A | 177 | 30.51 | 1.2 | 1.1 |
| S177C | 177 | 34.40 | 1.3 | 1.3 |
| S177D | 177 | 53.78 | 2.0 | 2.2 |
| S177E | 177 | 66.60 | 2.5 | 3.3 |
| S177Q | 177 | 36.42 | 1.4 | 1.3 |
| A180C | 180 | 42.73 | 1.6 | 1.6 |
| A180E | 180 | 59.70 | 2.3 | 2.6 |
| A180Q | 180 | 28.95 | 1.1 | 1.1 |
| S183D | 183 | 45.87 | 1.7 | 1.7 |
| S183E | 183 | 42.09 | 1.6 | 1.5 |
| S183P | 183 | 57.31 | 2.2 | 2.4 |
| K185G | 185 | 27.89 | 1.1 | 1.0 |
| Y196I | 196 | 46.85 | 1.7 | 1.7 |
| Y196V | 196 | 33.36 | 1.2 | 1.2 |
| K205A | 205 | 30.52 | 1.1 | 1.1 |
| K205L | 205 | 41.42 | 1.5 | 1.5 |
| N210A | 210 | 53.70 | 2.0 | 2.1 |
| N210G | 210 | 31.83 | 1.2 | 1.1 |
| N210S | 210 | 55.26 | 2.0 | 2.2 |
| Y226C | 226 | 37.04 | 1.2 | 1.1 |
| Y226G | 226 | 63.36 | 2.0 | 2.5 |
| Y226K | 226 | 42.08 | 1.3 | 1.3 |
| Y226N | 226 | 42.28 | 1.3 | 1.3 |
| Y226Q | 226 | 37.66 | 1.2 | 1.2 |
| Y226R | 226 | 49.66 | 1.5 | 1.6 |
| Y226S | 226 | 49.53 | 1.5 | 1.6 |
| Y226T | 226 | 35.42 | 1.1 | 1.1 |
| Y226W | 226 | 39.58 | 1.2 | 1.2 |
| D231P | 231 | 28.14 | 1.1 | 1.1 |
| D231T | 231 | 25.80 | 1.0 | 1.0 |
| R239Y | 239 | 33.11 | 1.3 | 1.3 |
| G245C | 245 | 50.30 | 1.6 | 1.7 |
| G245Q | 245 | 44.89 | 1.4 | 1.5 |
| S257A | 257 | 36.27 | 1.2 | 1.1 |
| S257C | 257 | 63.90 | 2.0 | 2.6 |
| S257D | 257 | 62.53 | 2.0 | 2.5 |
| S257E | 257 | 60.27 | 1.9 | 2.3 |
| S257F | 257 | 32.69 | 1.0 | 1.0 |
| S257G | 257 | 48.31 | 1.5 | 1.6 |
| S257H | 257 | 49.33 | 1.6 | 1.6 |
| S257K | 257 | 38.45 | 1.2 | 1.2 |
| S257P | 257 | 71.16 | 2.2 | 3.3 |
| S257V | 257 | 33.02 | 1.0 | 1.0 |
| L260K | 260 | 49.57 | 1.5 | 1.6 |
| L260M | 260 | 35.24 | 1.1 | 1.1 |
| L260Q | 260 | 40.30 | 1.2 | 1.2 |
| L260T | 260 | 36.35 | 1.1 | 1.1 |
| L260Y | 260 | 34.91 | 1.1 | 1.1 |
| T267D | 267 | 32.10 | 1.1 | 1.1 |
| T267E | 267 | 32.09 | 1.1 | 1.1 |
| N270C | 270 | 33.10 | 1.2 | 1.1 |
| N270D | 270 | 56.01 | 1.9 | 2.2 |
| S275A | 275 | 45.64 | 1.5 | 1.5 |
| S275D | 275 | 47.30 | 1.5 | 1.6 |
| S275E | 275 | 64.10 | 2.1 | 2.6 |
| S275P | 275 | 42.51 | 1.4 | 1.4 |
| N278D | 278 | 44.19 | 1.4 | 1.4 |
| N278E | 278 | 55.00 | 1.8 | 2.0 |
| N278W | 278 | 40.95 | 1.3 | 1.3 |
| N282C | 282 | 33.67 | 1.1 | 1.1 |
| N282F | 282 | 32.23 | 1.0 | 1.0 |
| N282Y | 282 | 48.83 | 1.6 | 1.6 |
| D283G | 283 | 49.09 | 1.6 | 1.7 |
| D283S | 283 | 40.92 | 1.6 | 1.5 |
| D283W | 283 | 38.86 | 1.5 | 1.4 |
| T284E | 284 | 26.34 | 1.0 | 1.0 |
| T284I | 284 | 28.69 | 1.1 | 1.1 |
| K288R | 288 | 27.45 | 1.0 | 1.0 |
| Q292M | 292 | 27.06 | 1.0 | 1.0 |
| Q292R | 292 | 26.70 | 1.0 | 1.0 |
| Q292V | 292 | 39.92 | 1.5 | 1.5 |
| K293I | 293 | 44.34 | 1.3 | 1.3 |
| K293L | 293 | 65.49 | 2.0 | 2.6 |
| K293P | 293 | 65.97 | 2.0 | 2.6 |
| K293R | 293 | 45.25 | 1.3 | 1.4 |
| G295S | 295 | 36.82 | 1.1 | 1.1 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

---

The invention claimed is:

1. An isolated mannanase variant, or recombinant polypeptide or an active fragment thereof comprising a modification at one or more positions corresponding to a position selected from the positions 101, 108, 132, 133, 177, 257 and 275 of the polypeptide of SEQ ID NO: 2, wherein each modification is independently a substitution, insertion, or deletion,
   wherein said variant, polypeptide or fragment thereof has at least 90% sequence identity but less than 100% sequence identity to the polypeptide of SEQ ID NO: 1 or the polypeptide of SEQ ID NO: 2,
   wherein said variant, polypeptide or fragment thereof has mannanase activity, and
   wherein said variant, polypeptide or fragment optionally further comprises a substitution, insertion, or deletion at one or more positions corresponding to a position selected from the positions 8, 9, 11, 13, 18, 21, 34, 37, 45, 47, 65, 100, 104, 107, 110, 114, 115, 116, 142, 147, 152, 154, 164, 169, 173, 174, 176, 180, 183, 185, 196, 199, 201, 202, 205, 206, 210, 215, 226, 229, 231, 239, 243, 245, 260, 267, 270, 278, 282, 283, 284, 288, 292, 293 and 295 of the polypeptide of SEQ ID NO: 2.

2. The variant, polypeptide, or fragment thereof according to claim 1, wherein said variant, polypeptide, or fragment thereof has an improved detergent stability, improved protease stability and/or improved thermostability compared to a parent polypeptide without any modification.

3. The variant, polypeptide, or fragment thereof according to claim 1, wherein said variant, polypeptide, or fragment thereof comprises a substitution or deletion at one position corresponding to positions 8, 9, 11, 13, 18, 21, 34, 37, 45, 47, 65, 100, 101, 104, 107, 108, 110, 114, 115, 116,132, 133, 142, 147, 152, 154, 164, 169, 173, 174, 176, 177, 180, 183, 185, 196, 199, 201, 202, 205, 206, 210, 215, 226, 229, 231, 239, 243,245, 257, 260, 267, 270, 275, 278, 282, 283, 284, 288, 292, 293,and 295 of the polypeptide of SEQ ID NO: 2, and wherein said substitution or deletion of the naturally-occurring amino acid residue at the one or more positions produces a mannanase variant having a HIF≥1.0 for a measure of stability at pH 8.0.

4. The variant, polypeptide, or fragment thereof according to claim 1, wherein said variant, polypeptide, or fragment thereof comprises one or more of the following substitutions versus the polypeptide of SEQ ID NO: 1 or the polypeptide of SEQ ID NO: 2: 58A, S8D, S8E, S8I, S8K, S8L, S8M, S8R, S8T, G9L, G9Q, G9R, G9S, G9V, G9W, G9Y, K11A, K11M, K11Q, K11R, K11S, K11V, Y13F, Y13I, Y13M, K18A, K18F, K18L, K18Q, K18R, K18S, V21I, V21M, N34C, N34E, N37C, N37D, N37H, N37Y, N37G, N37Q, K45A, K45C, K45D, K45E, K45G, K45H, K45M, K45N, K45Q, K45R, K45S, K45T, G47A, G47D, G47L, G47Q, G47R, G47S, D65P, D100G, D100K, D100L, A101C, A101E, A101L, A101N, A101M, A101Q, N104I, N104L, N104T, N104V, N104Y, N104C, N104M, N104Q, N104W, I107C, I107V, S108A, S108D, S108E, S108F, S108G, S108V, S108W, S108Y, K110A, K110G, K110H, K110N, K110Q, K110C, K110L, K110M, K110S, K110T, I114A, I114C, I114F, I114G, I114H, I114L, I114M, I114N, I114Q, I114R, I114T, I114V, I114W, I114Y, G115C, G115D, G115F, G115H, G115M, G115R, G115W, K116L, K116M, K116V, W132C, W132E, W132M, W132Q, W132Y, N133A, N133C, N133D, N133F, N133G, N133K, N133L, N133M, N133R, N133S, N133T, N133W, K142F, K142L, K142C, K142E, K142I, K142M, K142Q, K142R, K142V, K142W, K142Y, K147H, K147I, K147S, G152C, G152E, G152M, G152N, G152Q, G152R, G152S, K154A, K154D, K154E, K154F, K154G, K154H, K154L, K154M, K154T, K154W, W164D, W164F, W164M, W164Q, W164S, W164Y, Q169A, Q169M, D173C, D173E, Y174F, Q176A, Q176C, Q176E, Q176G, Q176H, Q176K, Q176L, Q176M, Q176R, Q176P, S177A, S177C, S177D, S177E, S177H, S177I, S177L, S177Q, S177R, S177T, S177V, A180E, A180Q, S183A, S183D, S183E, S183G, S183I, S183P, S183R, S183V, S183W, K185G, K185S, K185T, K185V, K185W, K185Y, Y196I, Y196V, K199A, A201E, A202C, A202K, A202M, A202P, A202R, A202W, K205A, K205C, K205D, K205L, K205N, K205S, A206L, A206M, A206F, A206T, N210A, N210G, N210S, G215M, Y226C, Y226G, Y226K, Y226N, Y226Q, Y226R, Y226S, Y226T, Y226W, N229C, D231P, D231T, R239F, R239Y, E243F, E243M, E243W, G245A, G245C, G245E, G245K, G245M, G245N, G245Q, G245R, S257A, S257C, S257D, S257E, S257G, S257H, S257K, S257P, S257V, L260C, L260F, L260K, L260M, L260Q, L260Y, L260T, T267D, T267E, N270A, N270C, N270D, S275A, S275D, S275E, S275K, S275P, S275Q, S275T, S275V, N278C, N278D, N278E, N278H, N278W, N282C, N282F, N282Y, D283G, D283S, D283W, T284E, T284I, K288A, K288R, Q292E, Q292I, Q292M, Q292R, Q292V, K293I, K293L, K293P, K293R, and G295S.

5. The variant, polypeptide, or fragment thereof according to claim 1, wherein a parent polypeptide has at least 59% sequence identity to the polypeptide of SEQ ID NO: 1 or the polypeptide of SEQ ID NO: 2.

6. The variant, polypeptide, or fragment thereof according to claim 5, wherein said parent polypeptide comprises or consists of the polypeptide of SEQ ID NO: 1 or SEQ ID NO: 2, or a fragment thereof having mannanase activity.

7. The variant, polypeptide, or fragment thereof according to claim 1, which has an improved property relative to a parent polypeptide, wherein said improved property is selected from the group consisting of catalytic efficiency, catalytic rate, chemical stability, oxidation stability, in-detergent stability, pH activity, pH stability, specific activity, stability under storage conditions, substrate binding, substrate cleavage, substrate specificity, substrate stability, surface properties, thermal activity, and thermostability.

8. The variant, polypeptide, or fragment thereof according to claim 1, wherein said mannanase activity is in the presence of a protease and/or a detergent component and/or detergent composition.

9. A composition comprising the variant, polypeptide, or fragment thereof according to claim 1, which is a cleaning or detergent composition comprising a surfactant, a bleaching system, a chelating agents, stabilizing agents, hydrotopes, builders, co-builders, bleach activators, polymers and/or fabric-huing agents.

10. The composition according to claim 9, wherein said composition further comprises an additional enzyme, optionally wherein said enzyme is a protease.

11. The composition according to claim 9, wherein said composition comprises a surfactant, wherein said surfactant is selected from the group consisting of anionic surfactants, cationic surfactants, nonionic surfactants, and amphoteric surfactants.

12. A method of dishwashing in an automatic dishwashing machine using the composition according to claim 9, comprising the steps of adding said composition in a detergent composition compartment in said automatic dishwashing machine, and releasing said composition during a main-wash cycle.

13. A method of laundering in an automatic laundering machine using the composition according to claim 9, comprising the steps of adding said composition in a detergent composition compartment in said automatic laundering machine, and releasing said composition during a main wash cycle.

* * * * *

UNITED STATES PATENT AND TRADEMARK OFFICE
CERTIFICATE OF CORRECTION

PATENT NO. : 11,535,837 B2
APPLICATION NO. : 17/041522
DATED : December 27, 2022
INVENTOR(S) : Rakhi Saikia et al.

It is certified that error appears in the above-identified patent and that said Letters Patent is hereby corrected as shown below:

In the Claims

Please amend Claim 4 at Column 81, Line 52 – Column 82, Line 44 as follows:
4. The variant, polypeptide, or fragment thereof according to claim 1, wherein said variant, polypeptide, or fragment thereof comprises one or more of the following substitutions versus the polypeptide of SEQ ID NO: 1 or the polypeptide of SEQ ID NO: 2: S8A, S8D, S8E, S8I, S8K, S8L, S8M, S8R, S8T, G9L, G9Q, G9R, G9S, G9V, G9W, G9Y, K11A, K11M, K11Q, K11R, K11S, K11V, Y13F, Y13I, Y13M, K18A, K18F, K18L, K18Q, K18R, K18S, V21I, V21M, N34C, N34E, N37C, N37D, N37H, N37Y, N37G, N37Q, K45A, K45C, K45D, K45E, K45G, K45H, K45M, K45N, K45Q, K45R, K45S, K45T, G47A, G47D, G47L, G47Q, G47R, G47S, D65P, D100G, D100K, D100L, A101C, A101E, A101L, A101N, A101M, A101Q, N104I, N104L, N104T, N104V, N104Y, N104C, N104M, N104Q, N104W, I107C, I107V, S108A, S108D, S108E, S108F, S108G, S108V, S108W, S108Y, K110A, K110G, K110H, K110N, K110Q, K110C, K110L, K110M, K110S, K110T, I114A, I114C, I114F, I114G, I114H, I114L, I114M, I114N, I114Q, I114R, I114T, I114V, I114W, I114Y, G115C, G115D, G115F, G115H, G115M, G115R, G115W, K116L, K116M, K116V, W132C, W132E, W132M, W132Q, W132Y, N133A, N133C, N133D, N133F, N133G, N133K, N133L, N133M, N133R, N133S, N133T, N133W, K142F, K142L, K142C, K142E, K142I, K142M, K142Q, K142R, K142V, K142W, K142Y, K147H, K147I, K147S, G152C, G152E, G152M, G152N, G152Q, G152R, G152S, K154A, K154D, K154E, K154F, K154G, K154H, K154L, K154M, K154T, K154W, W164D, W164F, W164M, W164Q, W164S, W164Y, Q169A, Q169M, D173C, D173E, Y174F, Q176A, Q176C, Q176E, Q176G, Q176H, Q176K, Q176L, Q176M, Q176R, Q176P, S177A, S177C, S177D, S177E, S177H, S177I, S177L, S177Q, S177R, S177T, S177V, A180E, A180Q, S183A, S183D, S183E, S183G, S183I, S183P, S183R, S183V, S183W, K185G, K185S, K185T, K185V, K185W, K185Y, Y196I, Y196V, K199A, A201E, A202C, A202K, A202M, A202P, A202R, A202W, K205A, K205C, K205D, K205L, K205N, K205S, A206L, A206M, A206F, A206T, N210A, N210G, N210S, G215M, Y226C, Y226G, Y226K, Y226N, Y226Q, Y226R, Y226S, Y226T, Y226W, N229C, D231P, D231T, R239F, R239Y, E243F, E243M, E243W, G245A, G245C, G245E, G245K, G245M, G245N, G245Q, G245R, S257A, S257C, S257D, S257E, S257G, S257H, S257K, S257P, S257V, L260C, L260F, L260K, L260M, L260Q, L260Y, L260T, T267D, T267E, N270A, N270C, N270D, S275A, S275D, S275E, S275K, S275P, S275Q, S275T, S275V, N278C, N278D, N278E, N278H, Signed and Sealed this
Thirteenth Day of August, 2024

*Katherine Kelly Vidal*

Katherine Kelly Vidal
*Director of the United States Patent and Trademark Office*

Page 1 of 2

N278W, N282C, N282F, N282Y, D283G, D283S, D283W, T284E, T284I, K288A, K288R, Q292E, Q292I, Q292M, Q292R, Q292V, K293I, K293L, K293P, K293R, and G295S.